US010059752B2

(12) United States Patent
McDermott et al.

(10) Patent No.: US 10,059,752 B2

(45) Date of Patent: Aug. 28, 2018

(54) ESCULENTIN 1A DERIVATIVES AND USES THEREOF

(71) Applicants: Alison McDermott, Bellaire, TX (US); Marialuisa Mangoni, Rome (IT)

(72) Inventors: Alison McDermott, Bellaire, TX (US); Marialuisa Mangoni, Rome (IT)

(73) Assignees: University of Houston System, Houston, TX (US); Universita' Degli Studi Di Roma La Sapienza, Rome (IT)

( * ) Notice: Subject to any disclaimer, the term of this patent is extended or adjusted under 35 U.S.C. 154(b) by 75 days.

(21) Appl. No.: 14/506,383

(22) Filed: Oct. 3, 2014

(65) Prior Publication Data

US 2015/0104492 A1 Apr. 16, 2015

Related U.S. Application Data

(60) Provisional application No. 61/890,521, filed on Oct. 14, 2013.

(51) Int. Cl.

| | |
|---|---|
| ***A61K 38/17*** | (2006.01) |
| ***A61K 45/06*** | (2006.01) |
| ***A61K 9/00*** | (2006.01) |
| ***C07K 14/46*** | (2006.01) |
| ***A61L 27/22*** | (2006.01) |
| ***A61L 27/34*** | (2006.01) |
| ***A61L 27/54*** | (2006.01) |
| ***A61L 29/04*** | (2006.01) |
| ***A61L 29/08*** | (2006.01) |
| ***A61L 29/16*** | (2006.01) |
| ***A61L 31/04*** | (2006.01) |
| ***A61L 31/10*** | (2006.01) |
| ***A61L 31/16*** | (2006.01) |

(52) U.S. Cl.

CPC ........ *C07K 14/463* (2013.01); *A61K 38/1703* (2013.01); *A61K 45/06* (2013.01); *A61L 27/22* (2013.01); *A61L 27/34* (2013.01); *A61L 27/54* (2013.01); *A61L 29/048* (2013.01); *A61L 29/085* (2013.01); *A61L 29/16* (2013.01); *A61L 31/047* (2013.01); *A61L 31/10* (2013.01); *A61L 31/16* (2013.01); *A61K 9/0051* (2013.01); *A61L 2300/25* (2013.01); *A61L 2300/252* (2013.01); *Y02A 50/473* (2018.01); *Y02A 50/475* (2018.01); *Y02A 50/478* (2018.01); *Y02A 50/481* (2018.01); *Y02A 50/483* (2018.01)

(58) Field of Classification Search

None

See application file for complete search history.

(56) References Cited

U.S. PATENT DOCUMENTS

2002/0035061 A1* 3/2002 Krieger .............. A61K 41/0028 514/2.4

OTHER PUBLICATIONS

Islas-Rodriguez et al., "Esculentin 1-21: a linear antimicrobial peptide from frog skin with inhibitory effect on bovine mastitis-causing bacteria," J. Peptide Sci. 15:607-14 (2009).*

Uccelletti et al., "Anti-Pseudomonas Activity of Frog Skin Antimicrobial Peptides in a Caenorhabditis elegans Infection Model: a Plausible Mode of Action In Vitro and In Vivo," Antimicrob. Agents Chemother. 54:3853-3860 (2010).*

Mahalakshimi et al., "The use of D-amino acids in peptide design," Chptr 5.9, pp. 415-430 of D-amino acids: A new frontier in amino acid and protein research, Nova Science Publ. Inc., 2006.*

Simmaco et al., "Antimicrobial Peptides From Skin Secretions of Rana Esculenta. Molecular Cloning of cDNAs Encoding Esculentin and Brevinins and Isolation of New Active Peptides," J. Biol. Chem. 269: 11956-11961 (1994).*

Parasitic Infections, Merck Manuals, accessed May 1, 2017 at URL merckmanuals.com/professional/infectious-diseases/approach-to-parasitic-infections/approach-to-parasitic-infections, pp. 1-13.*

Overview of Viruses, Merck Manuals, accessed May 1, 2017 at URL merckmanuals.com/professional/infectious-diseases/viruses/overview-of-viruses, pp. 1-5.*

* cited by examiner

*Primary Examiner* — Julie Ha

*Assistant Examiner* — Kristina M Hellman

(74) *Attorney, Agent, or Firm* — Benjamin Aaron Adler

(57) ABSTRACT

The present invention provides synthetic antibacterial peptides comprising a sequence at least 80% identical to a sequence shown in SEQ ID NO: 2 or the diastereomer thereof with a sequence shown in SEQ ID NO: 3 or pharmaceutical compositions thereof. Also provided are methods for reducing the severity of microbe-induced inflammation and for stimulating wound healing via the synthetic antibacterial peptides. Further provided is a device having a surface with a coating comprising the synthetic antibacterial peptides.

12 Claims, 13 Drawing Sheets

Specification includes a Sequence Listing.

SEQUENCE LISTING

```
<160> NUMBER OF SEQ ID NOS: 3

<210> SEQ ID NO 1
<211> LENGTH: 46
<212> TYPE: PRT
<213> ORGANISM: Pelophylax lessonae/ridibundus
<220> FEATURE:
<223> OTHER INFORMATION: sequence of esculentin 1a protein
<220> FEATURE:
<221> NAME/KEY: MISC_FEATURE
<222> LOCATION: 40, 46
<223> OTHER INFORMATION: cysteine at residues 40 and 46 form a
      disulphide bridge

<400> SEQUENCE: 1

Gly Ile Phe Ser Lys Leu Ala Gly Lys Lys Ile Lys Asn Leu Leu Ile
1               5                   10                  15
```

-continued

```
Ser Gly Leu Lys Asn Val Gly Lys Glu Val Gly Met Asp Val Val Arg
            20                  25                  30

Thr Gly Ile Asp Ile Ala Gly Cys Lys Ile Lys Gly Glu Cys
        35                  40                  45


<210> SEQ ID NO 2
<211> LENGTH: 21
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: 21
<223> OTHER INFORMATION: Gly at position 21 is amidated

<400> SEQUENCE: 2

Gly Ile Phe Ser Lys Leu Ala Gly Lys Lys Ile Lys Asn Leu Leu Ile
1               5                   10                  15

Ser Gly Leu Lys Gly
            20


<210> SEQ ID NO 3
<211> LENGTH: 21
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: 21
<223> OTHER INFORMATION: Gly at position 21 is amidated
<220> FEATURE:
<221> NAME/KEY: MISC_FEATURE
<222> LOCATION: 14,17
<223> OTHER INFORMATION: Leu at position 14 and Ser at position 17 are
      D-amino acids

<400> SEQUENCE: 3

Gly Ile Phe Ser Lys Leu Ala Gly Lys Lys Ile Lys Asn Leu Leu Ile
1               5                   10                  15

Ser Gly Leu Lys Gly
            20
```

ESCULENTIN 1A DERIVATIVES AND USES THEREOF

CROSS-REFERENCE TO RELATED APPLICATION

This nonprovisional application claims benefit of priority under 35 U.S.C. § 119(e) of provisional application U.S. Ser. No. 61/890,521, filed Oct. 14, 2013, now abandoned, the entirety of which is hereby incorporated by reference.

BACKGROUND OF THE INVENTION

Field of the Invention

The present invention is in the field of biology and medicine of microbial infections, for example, of the eye. More specifically, the present invention is directed to the novel use of esculentin 1a and derivatives thereof for the treatment of microbial keratitis.

Description of the Related Art

Microbial keratitis is a vision threatening infection of the cornea. It may be caused by bacterial, fungal, acanthamoeba or viral infection. Contact lens wear is a major factor that increases the risk of bacterial, fungal and acanthamoeba keratitis and millions of users around the world are at risk. As with all infections, causative organisms now commonly show resistance to traditional antimicrobial agents limiting the treatment options. Antimicrobial peptides are small peptides with potent activity against bacteria, fungi and some protozoa and viruses and are recognized to have a low risk for selecting for resistant organisms.

The prior art is deficient in use of Esculentin 1a and derivatives thereof for the treatment and prevention of microbial keratitis. The present invention fulfills this long-standing need and desire in the art.

SUMMARY OF THE INVENTION

The present invention provides for synthetic antibacterial peptides, for example, Esc-1a(1-21)$NH_2$ or the diastereoisomer thereof Esc-1a(1-21)1c$NH_2$ that are at least 80%, 90% or 95% thereto.

The present invention also provides for pharmaceutical compositions comprising the synthetic antibacterial peptides described herein and a pharmaceutically acceptable carrier.

The present invention also provides for related pharmaceutical compositions further comprising one or more of an antibacterial compound, an antiparasitic compound, an anti-acanthamoebal compound, an antifungal compound and an antiviral compound.

It is an object of the present invention to provide for the use of the synthetic antibacterial peptides or pharmaceutical compositions described herein to reduce the severity of microbe-induce inflammation via contact with the microbes.

It is another object of the present invention to further contact the microbes with one or more of an antibacterial compound, an antiparasitic compound, an anti-acanthamoebal compound, an antifungal compound and an antiviral compound to reduce the severity of microbe-induce inflammation.

It is an object of the present invention to provide for the use of the synthetic antibacterial peptides or pharmaceutical compositions described herein to stimulate wound healing via contact therewith.

It is another object of the present invention to provide a device having at least one surface comprising a coating of an effective amount of the synthetic antibacterial peptides described herein for the prevention of adhesion of pathogens to the device.

It is a further object of the present invention to demonstrate methods of delivery of the synthetic peptides or pharmaceutical compositions thereof described herein, such as via dendrimers and liposomes, and tethering of the peptide to surfaces to improve the effects in vivo.

Other and further aspects, features and advantages of the present invention will be apparent from the following description of the presently preferred embodiments of the invention. These embodiments are given for the purpose of disclosure.

BRIEF DESCRIPTION OF THE DRAWINGS

FIG. 1A: Bacterial cells were incubated with different concentrations of Esc-1a(1-21)$NH_2$ in the presence of 150 mM NaCl for 20 minutes at 37° C. Mean data from three experiments, expressed as the percentage of bacteria killed by the peptide with respect to the control sample (bacteria not treated with the peptide) are reported. FIG. 1B: Bacterial cells were incubated with the peptide (1 μM) in the absence or in the presence of varying concentrations of NaCl at 37° C. for 20 minutes. Mean data from three experiments, expressed as the percentage of bacteria killed by the peptide with respect to the control sample (bacteria not treated with the peptide) are reported.

FIG. 3A: Bacterial cells were incubated with 10 μM or 20 μM peptide in the presence of 50% reflex tears induced by onion vapors and pooled from three consenting adult volunteers with a normal ocular surface. FIG. 3B: Bacteria were incubated with 20 μM peptide in the presence of 70% reflex tears. In both cases, aliquots were withdrawn for cell counting at different time intervals. Mean data, expressed as the percentage of bacteria killed by the peptide are shown.

DETAILED DESCRIPTION OF THE PRESENT INVENTION

I. Definitions

Figure 1A:
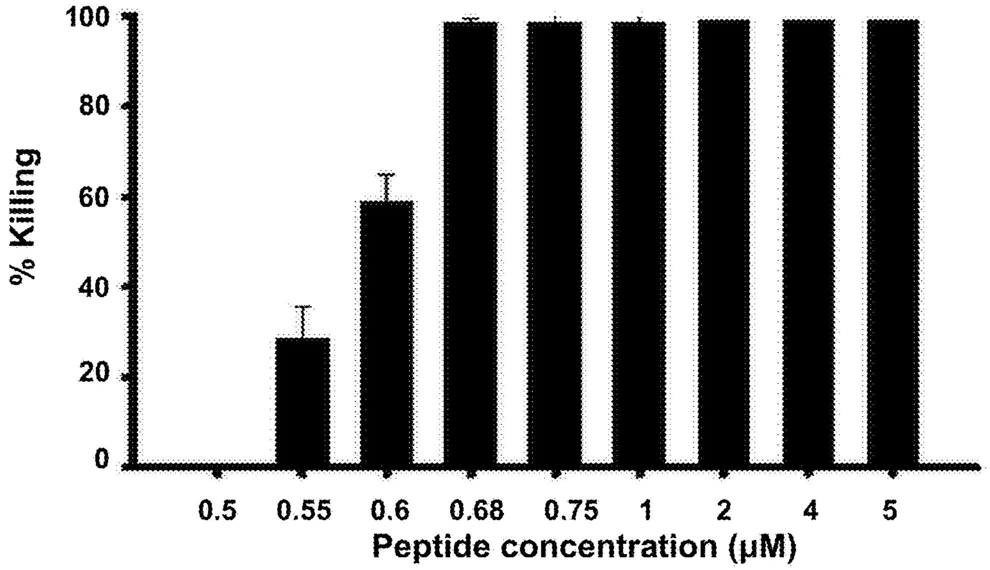
FIGS. 1A-1B show the effects of salt on the bactericidal activity of Esc-1a(1-21)$NH_2$ against *P. aeruginosa* ATCC 27853.

Unless otherwise noted, technical terms are used according to conventional usage. Definitions of common scientific technical terms may be found, for example, in McGraw-Hill Dictionary of Scientific & Technical Terms published by McGraw-Hill Healthcare Management Group; Benjamin Lewin, Genes VIII, published by Oxford University Press; Kendrew et al. (eds.), The Encyclopedia of Molecular Biology, published by Blackwell Publishers; and Robert A. Meyers (ed.), Molecular Biology and Biotechnology: a Comprehensive Desk Reference, published by Wiley, John & Sons, Inc; and other similar technical references.

As used herein the specification, "a" or "an" may mean one or more. As used herein in the claim(s), when used in conjunction with the word "comprising", the words "a" or "an" may mean one or more than one. As used herein "another" may mean at least a second or more. Furthermore, unless otherwise required by context, singular terms shall include pluralities and plural terms shall include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "pharmacologically effective dose" (or a derivative or variation thereof) is an amount of Esculentin 1a and derivatives thereof or composition containing the same that alleviates, totally or partially, the pathophysiological effects of a treatment indication of the invention (including, for example, treatment of an infection or a subject at risk of developing an infection). Unless otherwise indicated when referring to the administration of Esculentin 1a and derivatives thereof or composition containing the same, the Esculentin 1a and derivatives thereof or composition containing the same is administered at a concentration that is a pharmacologically effective dose. A pharmacologically effective dose will depend upon, for example, subject size, gender, magnitude of the associated disease, condition, or injury, and genetic or non-genetic factors associated individual pharmacokinetic or pharmacodynamic properties of the administered Esculentin 1a and derivatives thereof or composition containing the same. For a given subject in need thereof, a pharmacologically effective dose can be determined by one of ordinary skill in the art and by methods known to one of ordinary skill in the art.

II. The Present Invention

Microbial keratitis is a vision threatening infection. In particular, millions of individuals who wear contact lenses are at increased risk for microbial keratitis. Esculentin 1a and derivatives thereof are a novel treatment/preventative for microbial keratitis. There have been no new classes of antimicrobial drugs for microbial keratitis for many years. Further, Esculentin 1a and its derivatives have potential to be used to coat a contact lens—the advantage here is that the peptide will kill an organism on contact so preventing it from being transferred to the eye and causing infection.

As with all infections, pathogens that cause microbial keratitis are rapidly developing resistance to traditional antibiotics. Because of their mechanism of action, antimicrobial peptides such as Esculentin 1a have a low risk of inducing microbial resistance. Many antimicrobial peptides are also effective against bacterial biofilms. Further, antimicrobial peptides have a broad spectrum of antimicrobial activity. Thus a single peptide may be able to treat bacterial, fungal and acanthamoeba (and possibly viral) infections whereas currently available agents are only effective against one type of pathogen. This is an advantage as in the early stages of infection it may be difficult for a clinician to diagnose the causative pathogen type and if they make the wrong decision and for example use an antibacterial drug when the causative agent is actually a fungus, valuable treatment time is lost and may lead to poor clinical outcome. Antimicrobial peptides such as Esculentin 1a also can modulate host immune responses and enhance wound healing so there is the added benefit of tissue repair along side the ability to directly kill pathogens.

The present invention is directed to a synthetic antibacterial peptide comprising a sequence at least 80% identical to the sequence of SEQ ID NO: 2 or the diastereomer thereof with the sequence shown in SEQ ID NO: 3. In another aspect, the peptide is at least 90% identical to the sequence of SEQ ID NO:2 or the diastereomer thereof with the sequence shown in SEQ ID NO: 3 or the peptide is at least 95% identical to the sequence SEQ ID NO: 2 or the diastereomer thereof with the sequence shown in SEQ ID NO: 3.

The present invention is also directed to a method of reducing the severity of microbe-induced inflammation, comprising the step of contacting the microbe with an amount of one or more of the synthetic peptides described herein that is effective to reduce the inflammation caused by the microbe or to inhibit the growth of the microbe. The peptides reduce the microbe-induced inflammation by inhibiting the growth of the microbe, killing the microbe, reducing inflammatory cytokine production induced by the microbe or increasing anti-inflammatory cytokine production from host immune cells, or a combination thereof. In one embodiment, the bacteria are gram negative bacteria. Representative gram negative bacteria include but are not limited to *Escherichia coli, Salmonella, Shigella, Pseudomonas, Moraxella, Helicobacter, Stenotrophomonas, Bdellovibrio*, acetic acid bacteria, *Legionella, Wolbachia, Neisseria gonorrhoeae, Neisseria meningitidis, Moraxella catarrhalis, Hemophilus influenzae, Klebsiella pneumoniae, Legionella pneumophila, Pseudomonas aeruginosa, Helicobacter pylori, Salmonella enteritidis, Salmonella typhi* and *Acinetobacter baumannii*. In another embodiment, the bacterium is a gram positive bacteria. Representative gram positive bacteria include but are not limited to *Streptococcus, Staphylococcus, Corynebacterium, Listeria, Bacillus* and *Clostridium*.

In other aspects of this method, the microbe is a fungus, an acanthamoeba, a parasite or a virus. In one embodiment of this method of the present invention, the method further comprises the step of contacting the microbe with one or more of an antibacterial compound, an antiparasitic compound, an antifungal compound, an anti-acanthamoebal compound and an antiviral compound. Representative antiparasitic compounds include but are not limited to benzazole, an azole, a macrocycle, pyrantel pamoate, diethylcarbamazine, niclosamide, praziquantel, melarsopro, and eflornithine. Representative anti-acanthamoeba compounds include but are not limited to chlorohexidine and polyhexamethylene biguanide. Representative antiviral compounds include but are not limited to a nucleoside analog reverse transcriptase inhibitor, an uncoating inhibitor, a protease inhibitor, zanamivir, oseltamivir, and rifampin. Representative antibacterial compounds include but are not limited to an aminoglycoside, a beta-lactam, a cephalosporin, a quinolone, a macrolide, an oxazolidinone, an ansamycin, a sulphonamide, a tetracycline, a glycopeptide, a parahydroxy benzoic acid ester, sulfisoxazole, trimethoprim, novobiocin, daptomycin and linezolid. Representative antifungal compounds include but are not limited to an azole, a macrocycle, an allyl amine, an echinocandin, polygodial, ciclopirox, tolnaftate, benzoic acid, undecylenic acid, flucytosine and griseofulvin. In this method, the peptide may be in the form of a solid, an ointment, a gel, a liquid, an aerosol, a mist, a polymer, a contact lens, a film, an emulsion, or a suspension. In one preferred embodiment of this method, the composition is administered topically. In another preferred embodiment of this method, the peptide is incorporated into a sustained-release carrier. Representative sustained-release carriers include but are not limited to a sustained release polymer, a nanoparticle, a nanosuspension, a liposome and a microcapsule.

The present invention is further directed to a pharmaceutical composition comprising the synthetic antibacterial peptides described herein and a pharmaceutically acceptable carrier. This pharmaceutical composition may further comprise one or more of an antibacterial compound, an anti-parasitic compound, an anti-acanthamoebal compound, an antifungal compound and an antiviral compound.

The present invention is directed further to a device having at least one surface which comprises a coating containing an effective amount of a synthetic antibacterial peptide comprising a sequence at least 80% identical to the sequence of SEQ ID NO: 2 or the diastereomer thereof with the sequence shown in SEQ ID NO: 3. Representative examples of devices include but are not limited to catheters, implants, stents, fluid collection bags, sensors, hydrogel bandages, tubing, carriers for antibiotic, diagnostic and therapeutic agents, and ophthalmic devices. In one preferred aspect, the ophthalmic device is a contact lens. In another aspect, the device has a surface, which further comprises a polymer selected from the group consisting of hydrogels, silicone hydrogels, polymers and copolymers of 2-hydroxyethylmethacrylate and mixtures thereof.

The present invention is further directed to a method for stimulating wound healing, comprising the step of contacting the wound with an amount of one or more of the synthetic antibacterial peptides described herein. As a non-limiting example, the wound healing comprises a process of cell migration such as corneal epithelial cell migration, lung epithelial cell migration or HaCaT cell migration.

As would be well known to those having ordinary skill in this art, the antimicrobial peptide of the present invention may be manipulated to enhance activity. For example, it is well known that if the positive charge of a peptide is increased, activity can be enhanced. In other embodiments, the compounds of the invention comprise one or more conservative amino acid substitutions. Conservative substitutions, in which an amino acid is exchanged for another having similar properties, can be made in a compound of the invention by techniques well known by one of ordinary skill in the art. Conservative amino acid substitutions typically fall in the range of about 1 to 2 amino acid residues. Guidance in determining which amino acid residues can be substituted without activity or immunological properties can be found using computer programs well known in the art, such as DNASTAR software, or in Dayhoff et al. (1978) in Atlas of Protein Sequence and Structure (Natl. Biomed. Res. Found., Washington, D.C.). Amino acid substitutions conservative in nature are when, for example, the substituted amino acid has similar structural and/or chemical properties (including, for example, molecular weight, polarity, isoelectric point, hydrophilicity, hydrophobicity, charge, etc.) (see, for example, U.S. Pat. No. 7,098,015). Examples of conservative replacements are substitution of a leucine with an isoleucine or valine, an aspartate with a glutamate, or a threonine with a serine. Specifically, amino acids are generally divided into families: (1) acidic—aspartate and glutamate; (2) basic—lysine, arginine, histidine; (3) non-polar—alanine, valine, leucine, isoleucine, proline, phenylalanine, methionine, tryptophan; (4) uncharged polar—glycine, asparagine, glutamine, cysteine, serine threonine, and tyrosine; (5) aromatic amino acids—phenylalanine, tryptophan, and tyrosine.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Esculentin 1a and Esculentin 1a derived peptides

Esculentin 1a is a naturally occurring peptide found in the skin of the amphibian *Pelophylax lessonae/ridibundus* (formerly known as *Rana esculenta*). It is 46 amino acids in length and has an intramolecular disulphide bridge at the C-terminal end. The specific peptide used herein was Esc-1a(1-21)$NH_2$ which consists of the first 20 amino acids of the mature Esculentin 1a sequence with a glycinamide residue at the C-terminus. The single letter amino acid sequences are listed below:

```
Esculentin 1a:
                                          (SEQ ID NO: 1)
GIFSKLAGKKIKNLLISGLKNVGKEVGMDVVRTGIDIAGCKIKGEC;
and

Esculentin-1a(1-21)NH2:
                                          (SEQ ID NO: 2)
GIFSKLAGKKIKNLLISGLKG-NH2.
```

Novel Aspects and Unique Features

Esculentin1a is one of a very large peptide family referred to as antimicrobial peptides (AMPs). AMPs are produced by most living species including bacteria, invertebrates, vertebrates and plants and are a component of the natural defense systems of these species, being active against bacteria, fungi and some protozoa and viruses. In addition to a direct killing ability in humans, the peptides also have other actions including modulation of immune responses and wound healing. The key features that make an AMP useful as an antimicrobial agent are broad-spectrum activity, effective against planktonic and sessile states and reduced risk of pathogen resistance.

Broad-spectrum activity means that the peptides have antimicrobial activity against multiple types of pathogens. Thus, a given antimicrobial peptide may have activity against Gram positive and Gram-negative bacteria, fungi, acanthamoeba and even some viruses. This is generally not the case with traditional antimicrobial agents. The latter (e.g. penicillin, fluoroquinolones) may have activity against Gram negative and/or positive bacteria but they do not have anti-fungal activity. Prescribing pharmaceuticals for most infections is performed empirically, i.e., the doctor uses their knowledge and experience of the pathogens known to typically cause a particular infection to decide what antimicrobial agent to prescribe. In other words, the prescribing physician does not know for certain what the causative organism is. In the vast majority of cases this is not problem. However it is not uncommon for a physician to empirically prescribe a treatment and then find that it does not work indicating that either the expected causative organism has become resistant (see below) or that the infection is caused by some other type of pathogen. In the case of microbial keratitis caused by contact lens wear, Gram negative bacteria are the most common cause but certain fungi and acanthamoeba may also be responsible. Thus, in the typical scenario an eye doctor would prescribe an antibiotic but if it does not help resolve the infection this indicates that the probable cause is not bacterial but may be fungal so an antifungal agent would then be prescribed. Unfortunately, this practice results in time lost treating the patient with an ineffective medication, which may have adverse effects on the final outcome of treatment. Use of an agent, such as an AMP, with activity against bacteria and fungi, would mean there would be no delay in getting an effective treatment and improve the probability of a favorable outcome.

Importantly, several bacterial species e.g., *Pseudomonas aeruginosa* have the tendency to adhere to biological or inert surfaces (e.g. contact lens) and form sessile communities, named biofilms, which are very difficult to eradicate using traditional antibiotics. Some AMPs, including Esc-1a(1-21)$NH_2$, have been found to be active against both free-living (planktonic) and biofilm forms of this pathogen and thus its activity is improved over many traditional antibiotics.

It is well recognized that use of antimicrobial agents leads to the emergence of resistant pathogens. This is a particular problem with bacteria. Although there are a small number of pathogens that are naturally resistant to AMPs, the vast majority of pathogens are susceptible. AMPs are ancient components of the innate immune system, and they have retained their effectiveness over that time despite numerous interactions with pathogens. The reason for this, i.e., why AMPs are generally not associated with microbial resistance lies in their mechanism of action. Antimicrobial peptides primarily exert their antimicrobial activity by interacting with and disrupting microbial cell membranes. They do this by virtue of their overall positive charge, which allows them to interact electrostatically with the negatively charged microbial membrane without involving the recognition of chiral targets (e.g. membrane proteins). The microbial membrane is an essential component of the organism and to modify it in such a way as to prevent an antimicrobial peptide from interacting with it would severely compromise the organism. This contrasts with the mechanism of action of most traditional antimicrobial agents, which act by inhibiting enzymes, which are usually highly sensitive to mutation.

Another feature of antimicrobial peptides that may be of value is that many modulate immune responses, neutralize the toxic effect of the bacterial lipopolysaccharide (LPS), preventing the induction of septic shock from LPS-activated immune cells by reducing the level of pro-inflammatory cytokines such as TNFα and enhance wound healing. Thus, while one can envisage broad-spectrum activity and lack of resistance as the primary benefit of antimicrobial peptides they may also facilitate favorable resolution of microbial keratitis through additional effects on the ocular immune response and wound healing processes.

Uses

The present invention teaches the use of Esculentin1a and derivatives thereof for the treatment and/or prevention of microbial keratitis (infection of the cornea of the eye). For treatment, a representative example includes but is not limited to a topical formulation applied drop-wise to the eye. The topical formulation may simply be the Esculentin1a and derivatives thereof in a suitable solution compatible with use on the ocular surface. The topical formulation may also be more sophisticated such as delivery via nanoparticles such as dendrimers or liposomes, or a gel like solution. The rationale for the alternative delivery is to enhance the effectiveness of the peptide and improve retention time on the eye. Delivery via a specialized therapeutic contact lens, which delivers drug to the surface of the eye over time, would be readily recognized by a person having ordinary skill in this art.

For prevention of microbial keratitis, one could envisage the peptide covalently tethered to a contact lens. Contact lens wear is a major risk factor for microbial (particularly bacterial) keratitis. In the disease process, the contact lens becomes colonized with pathogens, which are then transferred to the eye when the lens is inserted. Wear of a contact lens is associated with compromise of multiple actions normally used by the surface of the eye to protect itself from infection. Thus, in contact lens wear, the defenses of the eye are reduced allowing the pathogen transferred from the contact lens to take hold. The tethering of peptide to create a so-called "antimicrobial contact lens" would mean that any pathogen trying to adhere to the lens is immediately killed by the peptide. Thus colonization of the contact lens is prevented and it does not/cannot harbor any pathogens that could be transferred to the eye. While these indications are in the specific area of ocular surface infection, the broad-spectrum activity of Esculentin 1a lends itself to the treatment of a multitude of infections, including lung infections. As described above, treatment of other infections may be via traditional means or by a coating on other medical devices such as catheters. In addition, while the studies described herein were focused on the anti-infective properties of Esculentin1a, it may also be possible to use the peptide to improve wound healing.

EXAMPLE 1

Minimum Inhibitory Concentration Assays

To determine the minimum inhibitory concentration (MIC) of Esc(1-21) that causes total inhibition of microbial growth against *Pseudomonas aeruginosa* and Staphylococcal strains, the following experiment (using *P. aeruginosa* ATCC 19660 as an example) was performed. MIC was determined using the 96 well micro-plate dilution assay. The test was performed in triplicate wells and Esc-1a(1-21)$NH_2$ was serially diluted to give concentrations of 0.125 μM to 64 μM.

Day 1: Picked a colony from a *P. aeruginosa* ATCC19660 streak plate, inoculated in to nutrient broth and incubated overnight at 37° C. with shaking (250 rpm)

Day 2 Steps: Removed 100 μl of the bacterial suspension and inoculated into 50 ml of fresh broth. Incubated for 2.5 hours with vigorous shaking (250 rpm) at 37° C. to achieve mid-log phase growth. Centrifuged the 50 ml culture at 3100 g for 10 minutes; discarded supernatant and resuspended pellet in 2 ml Muller-Hinton broth (MHB). Adjusted the optical density (OD) of the bacterial culture to 0.2 at 620 nm (corresponds to $-10^7$ CFU/ml) and diluted to $2\times10^6$ CFU/ml using MHB media. Thawed an aliquot of the peptide on ice. Pipetted 90 μl of MHB into wells A1, B1 and C1 and 50 μl of MHB media into A2-C2 through A12-C12. Added 10 μl of Esc-1a(1-21)$NH_2$ into wells A1, B1 and C1 and performed serial twofold dilutions of peptide in a volume of 50 μl from column 1 to column 10 (i.e. transferred 50 μl from A1, B1 and C1 to A2, B2 and C2 and so on till A10-C10). Columns A11-C11 had bacteria only (positive control) and A12-C12 had MHB media only (negative control). Pipetted 50 μl of the diluted *P. aeruginosa* ATCC 19660 in to each well using a multichannel pipette (final concentration was $1\times10^5$ bacteria in 100 μl volume). Wrapped the plate using parafilm to prevent evaporation and incubated in a shaker incubator (150 rpm) at 37° C. for 18-24 h.

Day 3 Steps: Read the plate using the spectrophotometer at 590 nm after examining the plates visually for turbidity. Generated spot plates to check for bacterial growth by plating out the contents of the first 3 wells showing no visible growth of bacteria onto MHA plates. Plated dilutions in duplicate and incubated the plates at 37° C. for 18 hr.

Day 4: Counted the number of colonies on the agar plates and plotted the data.

Data obtained by visual and spectrophotometric observation were comparable and showed clear/non-turbid wells indicating no growth of *P. aeruginosa* ATCC19660 with 64, 32 and 16 μM peptide. However, wells containing Esc-1a (1-21)$NH_2$ at a concentration of 8, 4, 2, 1, 0.5 and 0 μM exhibited considerable turbidity indicating significant bacterial growth and therefore the MIC was 16 μM. As reported in Table 1, a lower MIC (4 μM) was displayed by this peptide against *P. aeruginosa* ATCC 27853. Furthermore, four *P. aeruginosa* clinical isolates from human ocular surface infections (keratitis and conjunctivitis) and with varying degrees of resistance to commonly used antibiotics were included for comparison, as well as three other bacterial strains belonging to *Staphylococcus* genus (i.e. *S. aureus, S. epidermidis, S. hominis*) which are relevant not only for cornea, but also for conjunctiva infections, and that may be encountered in the eye clinic. Importantly, Esc-1a (1-21)$NH_2$ was found to be active on the selected clinical isolates with MIC values measured in the range of 2-8 μM for *P. aeruginosa* strains compared with a MIC of 1 μM or 8 μM for *S. hominis* or *S. epidermidis*, respectively. An exception was given by *S. aureus* toward which a higher MIC (64 μM) was detected (Table 1).

TABLE 1

Antimicrobial activity of Esc-1a(1-21)$NH_2$ against reference and clinical isolates from human ocular surface infections, with varying degrees of antibiotic resistance

| Species and strains | Relevant features | MIC (μM) |
|---|---|---|
| Reference strains | | |
| *Pseudomonas aeruginosa* ATCC 27853[a] | Reference strain, wild type | 4 |
| *Pseudomonas aeruginosa* ATCC 19660 | Reference strain, wild type | 16 |
| Clinical ocular isolates[b] | | |
| *Pseudomonas aeruginosa* R1 | CAZ, GEN, IPM, TOB | 2 |
| *Pseudomonas aeruginosa*1 Rm | CAZ, CIP, CTX, FEP, GEN, PIP, SXT, TOB | 4 |
| *Pseudomonas aeruginosa* n. 2 ME | CAZ, IPM | 8 |
| *Pseudomonas aeruginosa* n.3 | IPM | 8 |
| *Staphylococcus epidermidis* n.21(326) ME | ERY, GEN, OXA, TET, TOB, VAN | 8 |
| *Staphylococcus hominis* n. 1 ME | AMP, ERY, GEN, RIF, TET, TOB | 1 |
| *Staphylococcus aureus* n.6 ME | TET, TOB, | 64 |

[a]Data were taken from Luca et al. Cell Mol Life Sci 2013, 70: 2773-2786.

[b]Relevant resistance traits are indicated as follows: AMP, ampicillin; CAZ, ceftazidime; CIP, ciprofloxacin; CTX, cefotaxime; ERY, erythromycin; FEP, cefepime; GEN, gentamicin; IPM, imipenem; OXA, oxacillin; PIP, piperacillin; RIF, rifampin SXT, trimethoprim-sulfamethoxazole; TET, tetracycline; TOB, tobramycin; VAN, vancomycin

EXAMPLE 2

Tear and Salt Effects on Esc-1a(1-21)$NH_2$ Activity

Figure 1B:
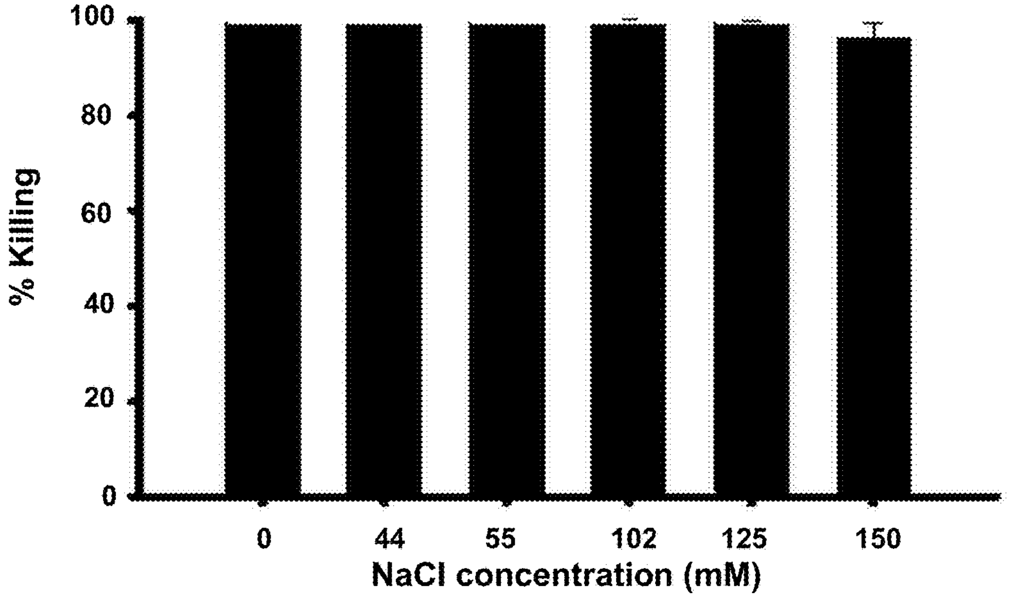

Owing to their mode of action, the antimicrobial activity of antimicrobial peptides may be reduced in the presence of salt. To demonstrate anti-Pseudomonal activity of Esc-1a(1-21)$NH_2$ in the presence of salt (NaCl), the following experiment was performed. In FIG. 1A $2\times10^6$ CFU/ml *P. aeruginosa* (ATCC 27853) were incubated with varying concentrations of Esc-1a(1-21)$NH_2$ in the presence of 150 mM NaCl at 37° C. for 20 min then aliquots plated and counted (n=3). In FIG. 1B, $2\times10^6$ CFU/ml *P. aeruginosa* (ATCC 27853) were incubated with 1 μM Esc-1a(1-21)$NH_2$ in the presence of increasing amounts of NaCl at 37° C. for 20 minutes then aliquots plated and counted (n=3). Concentrations of Esc-1a(1-21)$NH_2$ at 0.68 μM and above fully retained activity in 150 mM NaCl, the physiological salt concentration at the ocular surface.

Anti-Pseudomonal Activity of Esc-1a(1-21)$NH_2$ in the Presence of Basal Human Tears In addition to salt, mucins in tears have been shown to compromise the antimicrobial activity of some AMPs. $2\times10^6$ CFU/ml *P. aeruginosa* (ATCC 27853 or ATCC 19660) were incubated with 1-20 μM Esc-1a(1-21)$NH_2$ in the presence of 50% or 70% v/v tears and aliquots withdrawn, plated and counted after 30, 90 and 120 minutes (n=3).

Figure 2A:
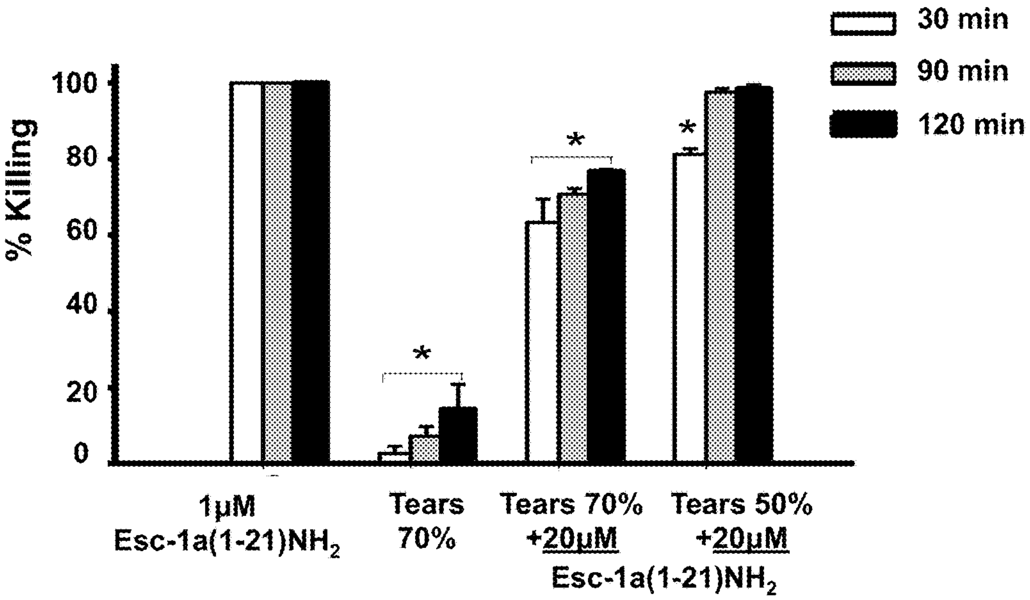
FIGS. 2A-2B show the effects of human basal tears on the bactericidal activity of Esc-1a(1-21)$NH_2$ against *P. aeruginosa* ATCC 27853 (FIG. 2A) and ATCC 19660 (FIG. 2B). Bacterial cells were incubated with the peptide in the presence of different concentrations of tears collected from eighteen consenting adult volunteers with normal ocular surface and pooled. Aliquots were withdrawn for cell counting at different time intervals. Mean data (n=3), expressed as the percentage of bacteria killed by the peptide are shown. *Indicates significant difference, $p<0.05$.
Figure 2B:
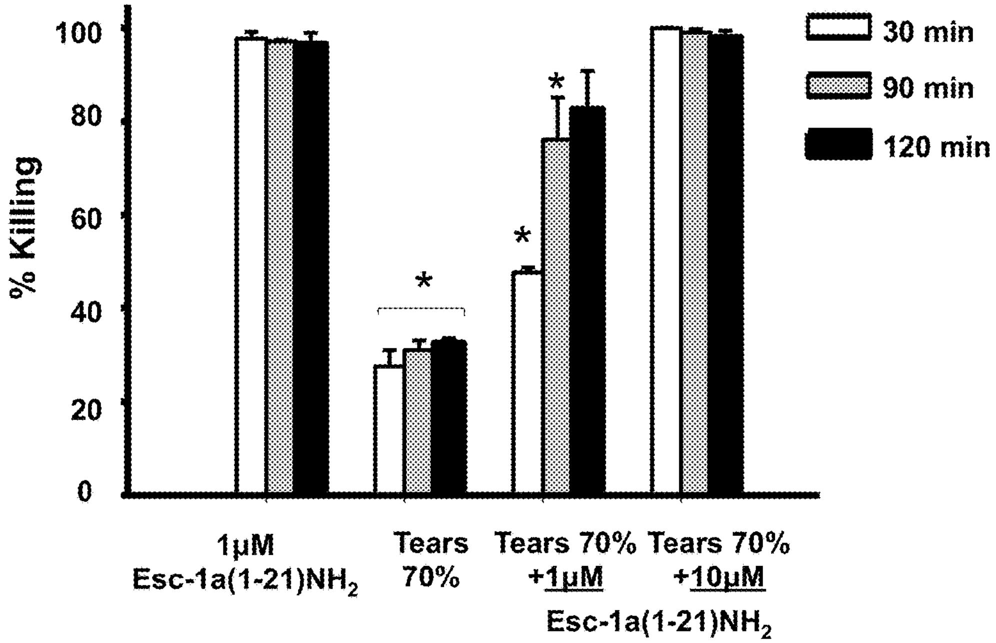

As can be seen in FIGS. 2A-2B, the majority of Esc-1a (1-21)$NH_2$ activity was retained in the presence of basal tears. There was 70% or 100% killing of strain ATCC 27853 after 90 minutes incubation with 20 μM Esc-1a(1-21)$NH_2$ (FIG. 2A) in 70% or 50% v/v tears. Also, although the MIC for Esc-1a(1-21)$NH_2$ was higher against ATCC19660 than ATCC 27853, 10 μM Esc-1a(1-21)$NH_2$ was sufficient to induce complete killing of *P. aeruginosa* ATCC19960 within 30 minutes in the presence of 70% (v/v) basal tears. As salt does not affect Esc-1a(1-21)$NH_2$ activity, the small reduction in activity in basal tears is presumed to be due to interaction with mucins.

Figure 3A:
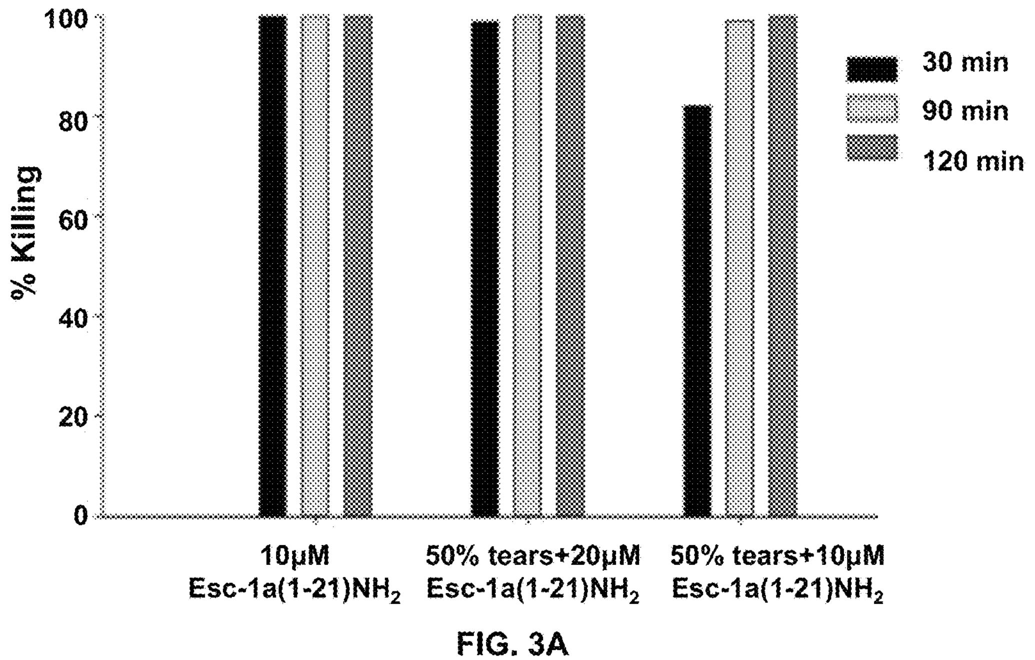
FIGS. 3A-3B shows the effects of human reflex tears on the bactericidal activity of Esc-1a(1-21)$NH_2$ against *P. aeruginosa* ATCC 27853.
Figure 3B:
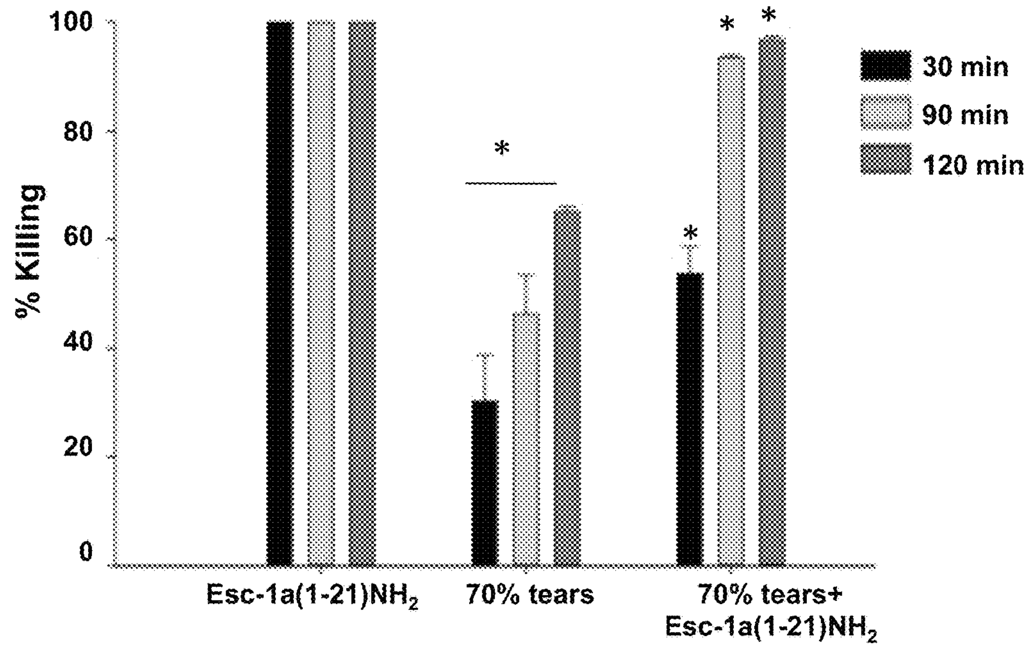

Anti-Pseudomonal Activity of Esc-1a(1-21)$H_2$ in the Presence of Reflex Human Tears $2\times10^6$ CFU/ml *P. aeruginosa* (ATCC 27853) were incubated with 10 μM or 20 μM Esc-1a(1-21)$NH_2$ in the presence of 50% (FIG. 3A) or 70% (FIG. 3B) human reflex tears and aliquots withdrawn, plated and counted after 30, 90 and 120 minutes (n=3). Esc-1a(1-21)$NH_2$ activity was retained in the presence of reflex tears.

EXAMPLE 3

MTT Cytotoxicity Assays

To determine the toxicity of Esc-1a(1-21)$NH_2$ to immortalized human telomerase corneal epithelial cells, the following experiment was performed. The MTT (3-(4,5-Dimethylthiazole-2-yl)-2,5-diphenyltetrazolium bromide) assay measures the activity of enzymes that reduce the tetrazolium blue dye to a formazan salt. Mitochondrial reductase enzymes will reduce MTT to formazan, which can be visualized by colorimetric reaction the absorbance of which can be quantified.

MTT assay was performed on human telomerase corneal epithelial cells treated with different concentrations of the peptide for 24 hrs. The test was performed in triplicate or quadruplicate wells with concentrations of the peptide of up to 100 μM using the following protocol. On day 1, plated the telomerase epithelial cells at 10,000 cells/well in a 96 well plate. Incubated the plate at 37° C. for 48 hrs to allow the cells to attach to the plate and spread. On day 2, incubated the cells in serum free media for at least 6 hrs prior to peptide treatment. On day 3, stimulated the cells with 100, 50, 25, 10, 5, 1, 0.5 and 0.1 μM Esc-1a(1-21)$NH_2$ in quadruplicate for 24 hrs. On day 4, added 50 μl of 0.02% Benzalkonium chloride into 4 wells as a positive control for 15 minutes. Added 50 μl of serum free media into all the other wells (total volume 100 μl). Added 10 μl of MTT stock solution into each of the well. Incubated at 37° C. for 3 hours. At the end of 3 hours purple crystals were visible under the microscope. Added 100 μl of stop solution into each well using a multichannel pipette. Pipetted up and down to dissolve all the crystals. Gently popped the bubbles using a 10 μl tip. Read plate using plate reader at 590 nm abs and 635 nm reference. Subtracted reference OD value (635) from 590 OD value and plotted graph.

Figure 4:
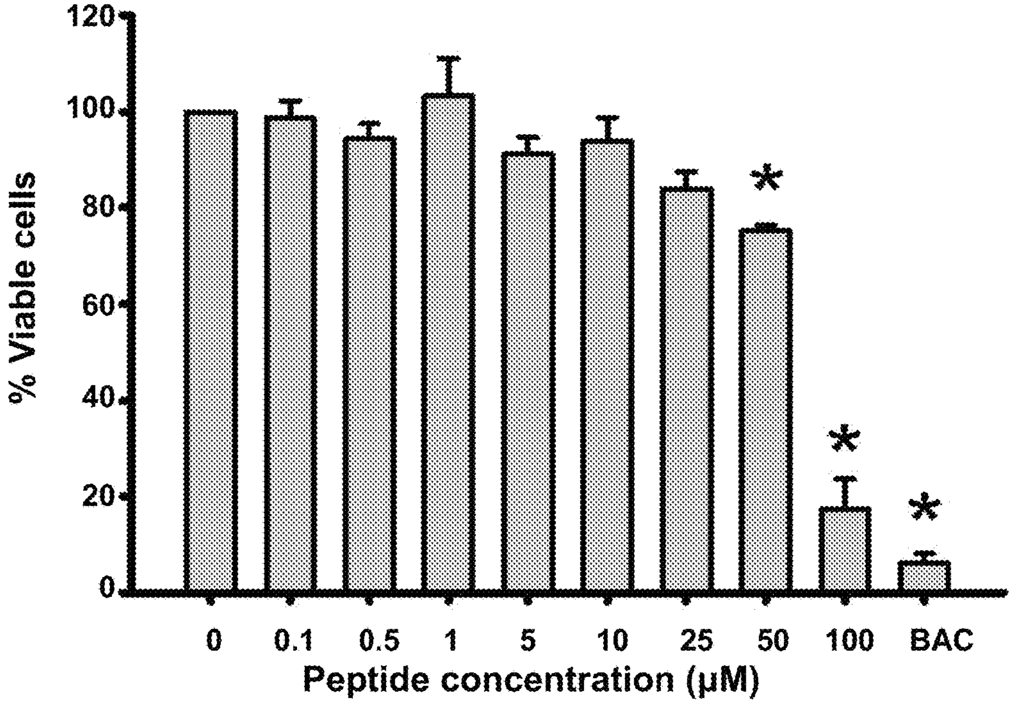
FIG. 4 shows the cytotoxicity of Esc-1a(1-21)$NH_2$ towards human corneal epithelial cells. Human corneal epithelial cells were incubated with varying concentrations of Esc-1a(1-21)$NH_2$ for 24 hrs then cytotoxicity determined by MTT assay. Data are the mean of 3 independent experiments. Esc-1a(1-21)$NH_2$ was significantly cytotoxic to corneal epithelial cells at concentrations above 50 μM. The positive control, benzalkonium chloride (BAC) caused almost 100% cytotoxicity. *Indicates $p<0.0002$ using ANOVA with Tukey's HSD for post hoc analysis.

Data from 3 experiments demonstrated that 100 μM and 50 μM of Esc-1a(1-21)$NH_2$ (mean of 9-12 wells from 3 different experiments) showed significant levels of toxicity compared to the lower concentrations of the peptide (FIG. 4). Concentrations lower than 50 μM did not show any significant levels of toxicity. The positive control BAC also showed a significant level of toxicity (6.2% viability) compared to untreated cells ($p<0.0013$). Data from 3 separate experiments indicated that Esc-1a(1-21)$NH_2$ at a concentration below 50 μM was not toxic to the cells. However, Esc-1a(1-21)$NH_2$ at 100 μM is definitely very cytotoxic (17.4% viability) to the telomerase corneal epithelial cells where as 50 μM peptide was slightly toxic (75.7% viability).

EXAMPLE 4

Clinical Grading, Neutrophil Infiltration and Viable Bacterial Counts Following Esc-1a(1-21)$NH_2$ Treatment in *Pseudomonas Aeruginosa* ATCC 19660 Induced Keratitis in C57BL/6 Mice To determine a clinical score, neutrophil infiltration by myeloperoxidase assay (MPO assay) and viable bacterial cell counts in infected and control corneas of C57BL/6 mice with *Pseudomonas aeruginosa* ATCC 19660 keratitis following pre-treatment and post-infection treatment with Esc-1a(1-21)$NH_2$ up to 5 days post-infection (PI) the following experiment was performed. In these experiments pre-treatment refers to a group of animals where treatment was initiated 24 hrs before infection then continued after infection.

Images of the uninfected control and infected eye were taken on days 1, 3 and 5 PI using a camera equipped slit lamp biomicroscope. Clinical grading of infection on days 1, 3 and 5 PI was by visualizing through a slit lamp and using an established grading scale (Table 2). These data are presented in FIG. 5. A myeloperoxidase assay was used to quantitate the polymorphonuclear cell numbers in the infected and control corneas (data presented in FIG. 6). Viable counts for bacteria were recovered from corneas at day 1, 3 and 5 PI (FIG. 7).

TABLE 2

Grading of slit lamp observations of ocular disease in *P. aeruginosa* infected mice

| Clinical Score/grade | Slit lamp observation |
|---|---|
| 0 | Clear or slight opacity, partially covering pupil. |
| 1 | Slight opacity fully covering cornea. |
| 2 | Dense opacity, partially or fully covering pupil. |
| 3 | Dense opacity, covering entire cornea. |
| 4 | Corneal perforation or phthisis. |

Mice Infection and Data Collection

1. IP injections of ketamine and xylazine mixture were given (final dose 100 and 10 mg/kg respectively) to anesthetize the mice.

2. Pre-treatment group—5 μl of peptide (40 μM) was instilled topically onto intact corneas—3 times in 24 h.

3. Day 0—Day of infection:

a. 3×1 mm parallel scratches were made at the center of the right cornea of the mice using a 27% gauge needle and 5 μl of *P. aeruginosa* ATCC19660 bacterial solution ($1\times10^6$ CFU) was pipetted on the wounded cornea.

b. Topically pipetted 5 μl of 40 μM Esc-1a(1-21)$NH_2$ or vehicle (PBS) on the cornea 2-times on Day 0 starting 5 hours after bacterial infection.

4. Day 1 post-infection:

a. Captured images and graded the infection using a slit lamp biomicroscope.

b. Harvested corneas from 2 mice per group, pooled the corneas and processed them to perform the MPO assay.

c. Instilled peptide or vehicle three times/24 hrs (6.30 am, 1.30 pm, 8.30 pm).

5. Repeated the peptide or vehicle treatment 3 times a day for the next 4 days.

6. In addition, captured images, graded the infection and repeated the MPO assay on Day 3 and 5 post-infection.

Myeloperoxidase Assay Protocol

An MPO assay was used to quantitate polymorphonuclear cell numbers in the cornea from both infected corneas (n=2/group/time point) of Esc-1a(1-21)$NH_2$ treated and control (PBS) treated animals. Briefly, corneas were harvested at days 1, 3 and 5 PI. The change in absorbance at 450 nm was monitored for one hour at 15-30 minute intervals. The results were expressed as units of MPO per cornea. One unit of MPO activity is equivalent to $2*10^5$ polymorphonuclear cells.

Harvested and pooled corneas (2 mice/group) in 200 μl of sterile PBS/cornea. Placed the harvested corneas on ice until further processing. Homogenized the corneas for 30-45 seconds and briefly sonicated them for 10-20 seconds.

A. Made up 50 mM $KH_2PO_4$ at pH 6.

B. Weighed out 0.00167 g of O-dianisidine dihydrochloride (O-d-d) (for 10 ml)

C. Added 10 μl of 0.5% HTAB (hexadecyltrimethylammonium bromide in potassium phosphate buffer 50 mM pH 6) to 90 μl homogenate (stored the remaining homogenate on ice to obtain recoverable *P. aeruginosa* counts for viability assay).

D. Sonicated samples 2×5 seconds then freeze thawed three times on liquid nitrogen.

E. Centrifuged at 14000*g at 4° C. for 20 minutes.

F. To 10 ml of phosphate buffer added 0.00167 g O-dianisidine dihydrochloride and 1.67 μl (0.05%) $H_2O_2$. 90 μl of this was added to each well to produce the color reaction (protected the solution from light).

G. Made up standards for MPO using phosphate buffer based on the initial concentration of the MPO. Double diluted 25 μl MPO standard & carry 25 μl over since 10 μl was needed per well (run in duplicate).

H. Added 10 μl of each standard to 96 well plate and 10 μl sample supernatant (in triplicate).

I. Added 90 μl phosphate buffer containing O-d-d and $H_2O_2$ to the plate. Popped bubbles and read on spectrophotometer at 450 nm at 3 minutes, 5 minutes, 10 minutes, 15 minutes, 30 minutes, 45 minutes and 60 minutes.

To quantitate viable bacteria, a 100 μl aliquot from the corneal homogenates was serially diluted 1:10 in sterile PBS. Duplicate aliquots (20 μl) of each dilution, including the original homogenate, were plated onto nutrient agar. Plates were incubated for 14-16 h at 37° C.

Clinical Grading of Infection

Figure 5:
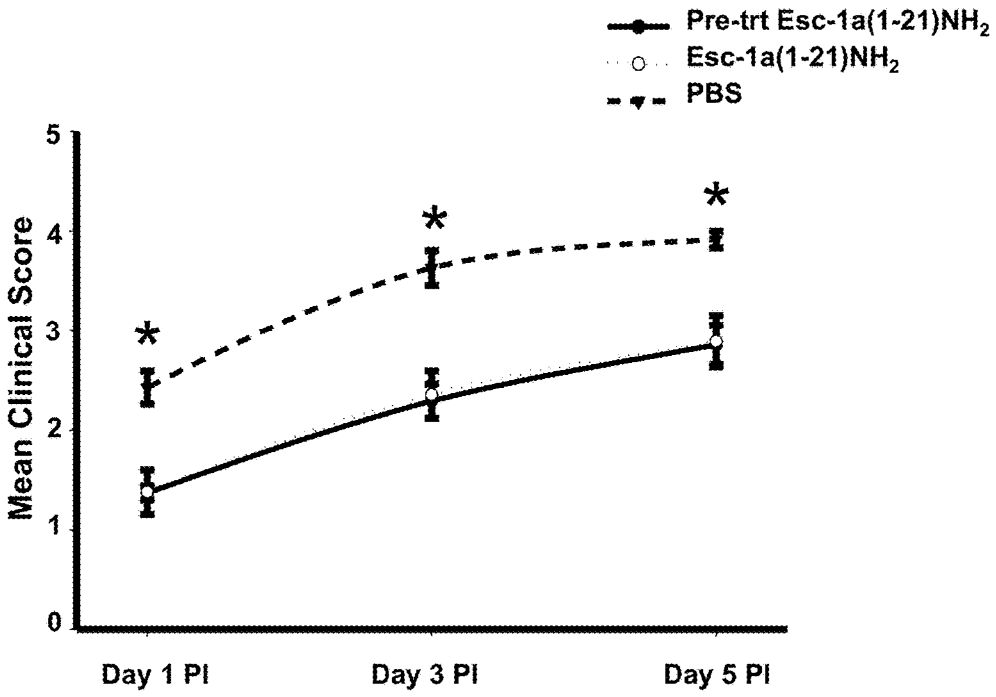
FIG. 5 shows that Esc-1a(1-21)$NH_2$ reduces severity of *Pseudomonas* keratitis in mice. C57BL/6 mice were infected in one eye with *P. aeruginosa* ATCC 19660 and treated with 40 uM Esc-1a(1-21)$NH_2$ or vehicle control (PBS). In some animals (Pre-trt group) treatment with Esc-1a(1-21)$NH_2$ was initiated 24 hrs prior to infection. Esc-1a(1-21)$NH_2$ treated animals had a significantly lower clinical score than PBS treated controls at each time point (data are average from 4 independent experiments with 4-6 mice/experiment). *Indicates significant difference, $p<0.05$, among control and peptide treated groups. There was no significant difference between the Esc-1a(1-21)$NH_2$ pretreatment group and when treatment was begun after infection.

The mean clinical scores for the Esc-1a(1-21)$NH_2$ treated and PBS vehicle control group at day 1, 3 and 5 PI obtained from 4 separate experiments where the size of inoculum was $1*10^6$ CFU/5 μl were plotted (FIG. 5).

Data are results from 4 independent experiments with 4-6 animals/treatment group. Esc-1a(1-21)$NH_2$ pre-treated mice had a mean clinical score of 1.37±0.07 at day 1 PI and 2.29±0.17, 2.86±0.20 at days 3 and 5 PI. The Esc-1a(1-21)$NH_2$ treated animals demonstrated a mean clinical score similar to the pre-treated animals of 1.38±0.22, 2.36±0.24 and 2.89±0.26 at day 1, 3 and 5 PI. The mean scores for the control PBS treated animals at days 1, 3 and 5 PI were 2.43±0.17, 3.63±0.17 and 3.92±0.08. Infection was significantly less severe at all time points ($p<0.009$, 0.005 and 0.009 at days 1, 3 and 5 PI respectively) for mice treated (or pretreated) with Esc-1a(1-21)$NH_2$. Data from the pre-treated and Esc-1a(1-21)$NH_2$ treated animals were not significantly different at day 1, 3 or 5 PI with $p<0.95$, 0.83 and 0.92 respectively. These data were consistent with the severity of ocular disease observed by comparing the captured images.

PMN Infiltration into the Cornea

Figure 6:
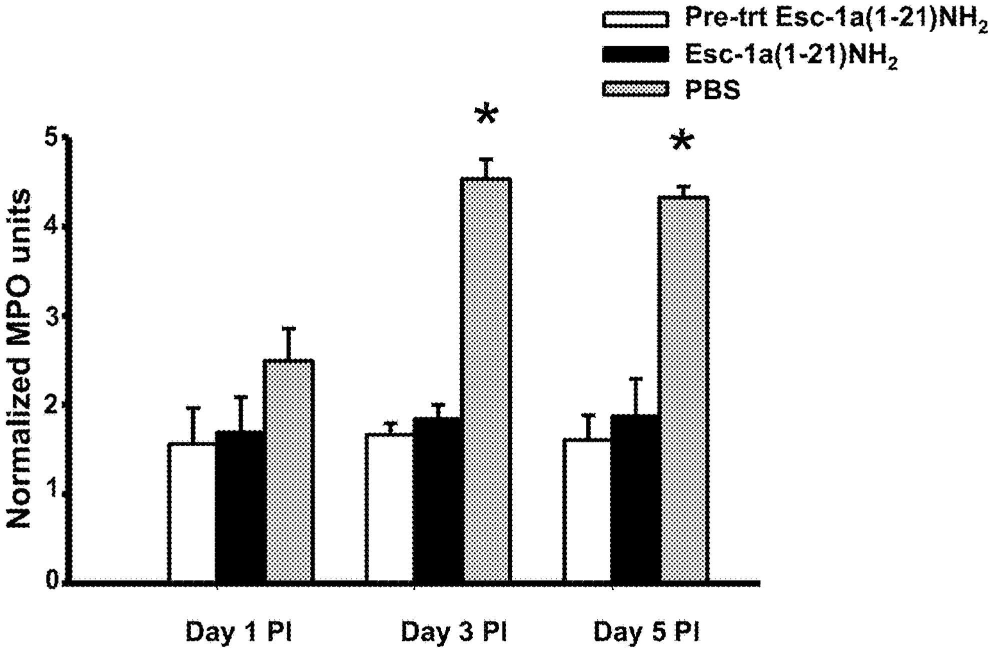
FIG. 6 shows reduced neutrophil infiltration in Esc-1a(1-21)$NH_2$ treated corneas. Corneas were harvested 1,3 and 5 days after infection and neutrophil infiltration determined by MPO assay. There was significantly greater neutrophil infiltration in PBS vehicle treated animals compared to Esc-1a (1-21)$NH_2$ treated animals on days 3 and 5 post infection (n=3). PI=post infection, Pre-trt=pretreatment with Esc-1a (1-21)$NH_2$. *Indicates significant difference, $p<0.05$, among PBS control and peptide treated groups.
Figure 7:
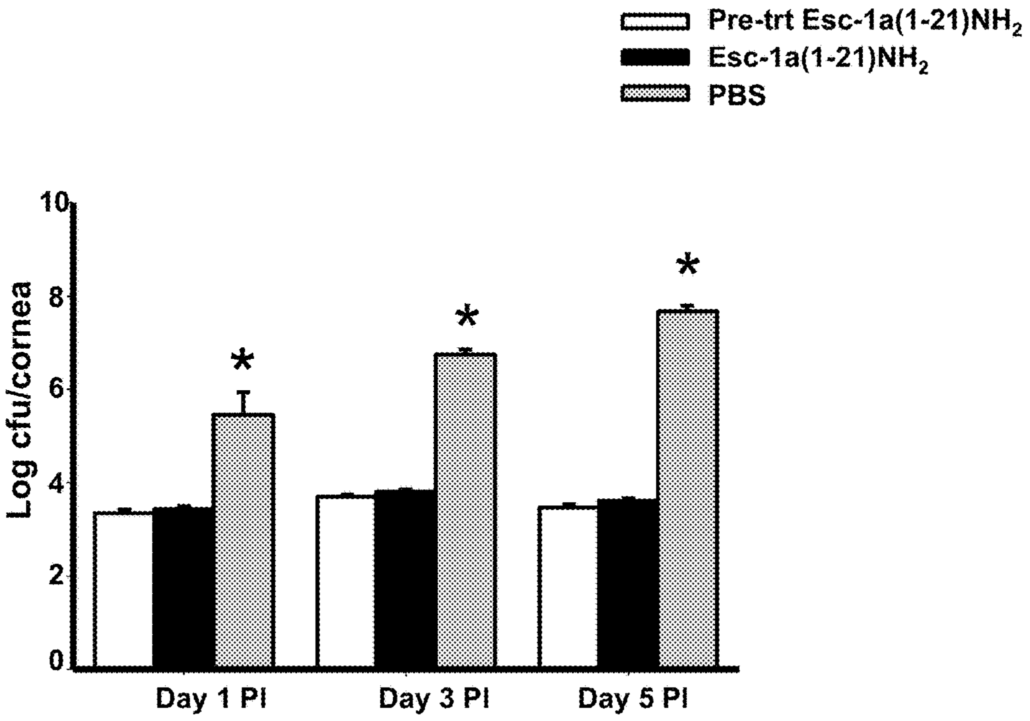
FIG. 7 shows reduced recovery of viable *P. aeruginosa* ATCC 19660 in Esc-1a(1-21)$NH_2$ treated corneas. Corneas were harvested 1, 3 and 5 days after infection and the number of surviving bacteria determined. At each day there were significantly greater numbers of bacteria in PBS vehicle treated animals compared to Esc-1a(1-21)$NH_2$ treated animals (n=3). PI=post infection; Pre-trt=pretreatment with Esc-1a(1-21)$NH_2$. *Indicates significant difference, $p<0.05$, among PBS control and peptide treated groups.
Figure 8A:
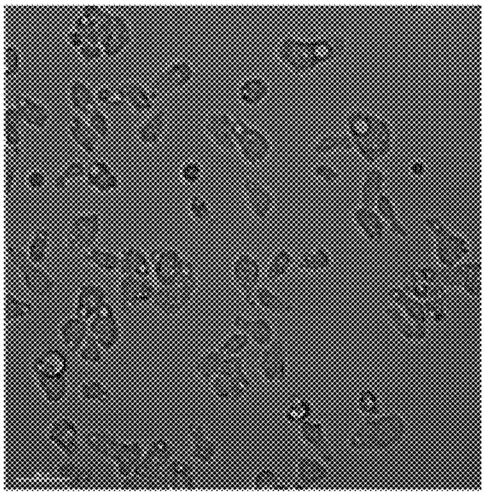
FIGS. 8A-8D shows the effect of Esc-1a(1-21)$NH_2$ on the viability of Acanthamoeba castellani. The amoeba were seeded in to chamber slides, then a fluorescent viability dye (ethidium homodimer-1) and 500mg/ml Esc-1a(1-21)$NH_2$ added. The amoebas were viewed by time lapse microscopy in an environmental chamber for 6 hours. Images are from before peptide addition at time zero in healthy trophozpites (FIG. 8A), then 10 minutes (FIG. 8B), 2 hours (FIG. 8C) and 6 hours (FIG. 8D) post peptide addition of Esc-1a(1-21) $NH_2$. The amoeba rapidly rounded up in response to the peptide and exhibited fluorescence (white) indicating dead/dying cells. Significant amounts of debris accumulated over time indicating rupture of the cells.
Figure 8B:
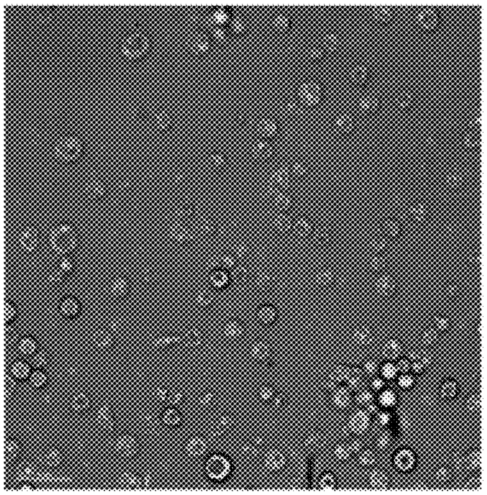
Figure 8C:
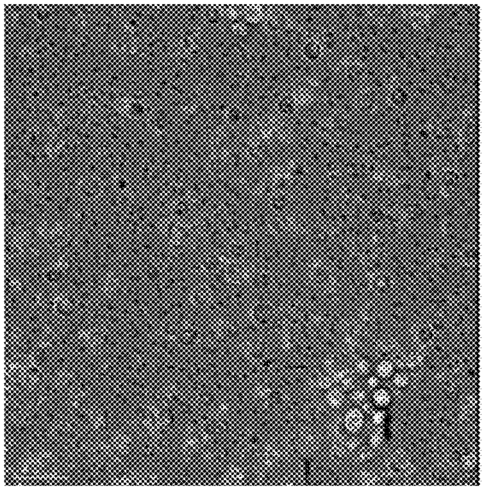
Figure 8D:
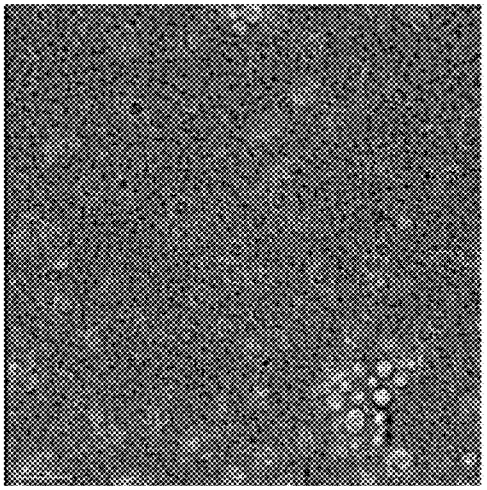

The MPO units per cornea were determined and the mean from 3 independent experiments was plotted (FIG. 6).

Normalized MPO data obtained indicate that Esc-1a(1-21)$NH_2$ pre-treated mice MPO activity was 1.55±0.4 at day 1 PI and 1.66±0.13, 1.55±0.28 at days 3 and 5 PI. The peptide treated animals had MPO units of 1.69±0.40, 1.84±0.16 and 1.82±0.42 at day 1, 3 and 5 PI. The normalized data for the PBS treated control animals at days 1, 3 and 5 PI were 2.5±0.36, 4.53±0.22 and 4.2±0.12. The normalized MPO units obtained for the uninfected left eye (of animals with infected right eye) in all treatment groups at all time points was not significantly different from uninfected control animal ($p<0.15$). Data from the Esc-1a(1-21)$NH_2$ pre-treated and Esc-1a(1-21)$NH_2$ treated animals were not significantly different at day 1, 3 or 5 PI with $p<0.83$, 0.42 and 0.62 respectively. The pre-treated and Esc-1a(1-21)$NH_2$ treated animals showed no significant difference in MPO values compared to the PBS treated controls at day 1 PI ($p<0.15$, 0.20). However, the MPO values and hence the number of polymorphonuclear cells recruited into the cornea were significantly lower in the pre-treated and Esc-1a(1-21)$NH_2$ treated animals compared to PBS control animals at days 3 and 5 PI ($p<0.0004$ and 0.0012 for the pretreated group and 0.0006 and 0.005 for the Esc-1a(1-21)$NH_2$ group). Additionally, the Esc-1a(1-21)$NH_2$ pre-treated and Esc-1a(1-21)$NH_2$ treated infected corneas showed no significant difference between each time point at day 1, 3 and 5 PI. However, the PBS treated control corneas demonstrated a significantly higher recruitment of inflammatory cells and hence a higher polymorphonuclear cell count at day 3 and day 5 PI compared to day 1 ($p<0.008$ and 0.008). There was no significant difference seen in the PBS treated corneas at day 3 and day 5 PI.

Viable Bacterial Count

The harvested corneas were homogenized, plated on growth media and the bacterial colonies recovered counted 14-18 hours post plating. Data plotted (FIG. 7) show the viable bacterial counts obtained from an average of 3 independent experiments.

Viable bacterial counts obtained for the PBS control group were significantly greater than for the Esc-1a(1-21)$NH_2$ pre-treated or treated groups at days 1, 3 and 5 PI ($p<0.001$, 0.0001, 0.0001 respectively) with a 2-3 $\log_{10}$ CFU difference at days 1 and 3 and 4 $\log_{10}$ at day 5 PI. There was no significant difference between the pretreated and Esc-1a(1-21)$NH_2$ treated infected corneas ($p<0.41$, 0.15 and 0.15) at days 1, 3 and 5 PI respectively. The pre-treated corneas showed a significantly higher CFU at day 3 PI (3.7 $\log_{10}$ CFU) compared to day 1 (3.35 $\log_{10}$ CFU) and day 5 PI (3.47 $\log_{10}$ CFU) ($p<0.01$ and 0.04 respectively). The peptide treated corneas demonstrated a similar pattern with statistically significant differences ($p<0.008$, 0.04 at day 1 and 5 PI respectively). However in PBS treated control animals there was a much greater increase in the viable bacteria recovered at day 3 PI (6.76 $\log_{10}$ CFU) compared to day 1 PI (5.8 $\log_{10}$ CFU) and for day 5 PI (7.7 $\log_{10}$ CFU) as compare to day 3 PI ($p<0.02$).

Overall the clinical score data show that Esc-1a(1-21)$NH_2$ significantly reduced the severity of *Pseudomonas aeruginosa* keratitis. There was no difference among the beneficial effects of Esc-1a(1-21)$NH_2$ if treatment was started before infection. Esc-1a(1-21)$NH_2$ treated animals showed a significantly lower number of inflammatory cells and reduced recoverable viable bacterial cells which contributed to the beneficial effects of the treatment.

EXAMPLE 5

Efficacy of Esc(1-21) against Acanthamoeba $1\times10^4$ *A. castellani* (ATCC 50370) trophozoites in PYG 712 growth medium were transferred to coverglass chamber slides and allowed to attach overnight. The cells were then incubated with PYG 712 medium containing a 1:100 dilution of ethidium homodimer-1 (EthD-1) for 15 minutes at room temperature. EthD-1 is a cell-impermeant viability indicator dye that is taken up by cells with a compromised plasma membrane and fluoresces red/orange when bound to DNA. Serial brightfield and fluorescence images were taken using a DeltaVision Spectris Core fluorescence microscope every 3 minutes for 30 minutes to visualize cellular health prior to addition of Esc-1a(1-21)$NH_2$. The medium was then replaced with 200 μl growth media containing 125, 250 or 500 μg/ml Esc-1a(1-21)$NH_2$ and 1:100 diluted ethidium homodimer-1. Brightfield and fluorescence images were taken every 3 minutes for another 6 hours. Serial images were compiled together using Softworx software (Applied Precision) to generate time-lapse videos.

Exposure to the peptide at 500 μg/ml (FIGS. 8A-8D) rapidly caused the trophozoites to round up and orange/red fluorescence could be detected within 10 minutes indicating the presence of dead/dying cells. Significant accumulation of debris due to cell rupture followed quickly. Similar effects were seen with the lower concentrations of Esc-1a(1-21)$NH_2$ although the time course for killing was longer. With 250 μg/ml Esc-1a(1-21)$NH_2$ approximately 82% and 100% of the trophozoites stained positively with EthD-1 at 10 minutes and 6 hours respectively. For 125 μg/ml Esc-1a(1-21)$NH_2$ approximately 67% of the trophozoites stained positively with EthD-1 at 6 hours. These results show that Esc-1a(1-21)$NH_2$ has potent and rapid killing activity against *A. castellani* and can be a therapeutic agent against this pathogen.

EXAMPLE 6

Effect of Esc-1a(1-21)$H_2$ on Wound Healing

Figure 9:
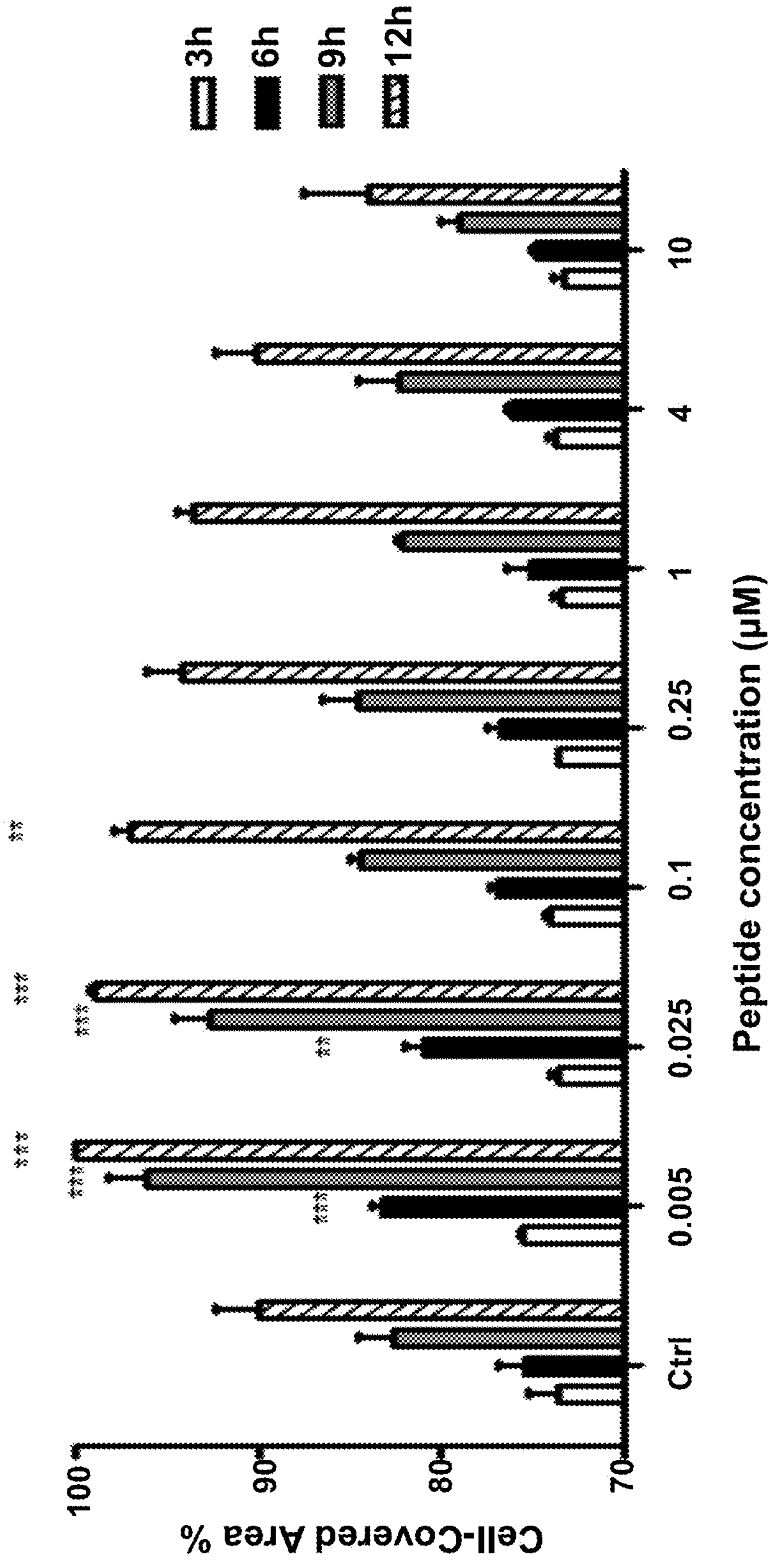
FIG. 9 shows the effect of Esc-1a(1-21)$NH_2$ on the closure of a wound field produced in a monolayer of corneal epithelial cells. The percentage of cell-covered area at each time point was determined and is reported on the y-axis. Control (Ctrl) represents cells not treated with the peptide. All data are the mean of at least three independent experiments ±SE. The levels of statistical significance between control and treated samples are indicated as follows:  $p<0.01$, *$p<0.001$.

To determine cell migration after treatment with Esc-1a(1-21)$NH_2$, a wound healing assay was performed using telomerase immortalized human corneal epithelial cells (hTCEpi) (FIG. 9). Cells were cultured in Keratinocyte growth Medium-2 supplemented with growth factors and Normocin 50 mg/ml (KGM-2g). Cell migration was studied as follows: hTCEPpi cells (70,000) suspended in KGM-2g were seeded on each side of ibidi culture inserts for live cell analysis (Ibidi, Munich, Germany). Inserts were placed into 35 mm dishes and incubated at 37° C. and 5% $CO_2$ to allow cells grow to confluence. Afterwards, inserts were removed with sterile tweezers to create a cell-free area ("wound") of approximately 500 μm; after a wash with 1 ml of PBS, 1 ml of Dulbecco's modified Eagle's medium (DMEM) supplemented with 4 mM L-glutamine, 5% fetal bovine serum (FBS) and the peptide at different concentrations was added. The dishes with inserts were placed in an appropriate incubator and the cells were allowed to migrate. At 0, 3, 6, 9 and 12 hours, fields of the injury area were visualized microscopically under an inverted microscope (Olympus CKX41) at ×4 magnification and photographed with a Color View II digital camera. The percentage of cell-covered area at each time was determined by WIMASIS Image Analysis program. Esc-1a(1-21)$NH_2$ was diluted in $H_2O$ to 2 mM stock concentration and aliquots were stored at −20° C.

Esc-1a(1-21)$NH_2$ significantly stimulated cell migration within 6, 9 and 12 h, at a concentration range from 0.005 μM to 0.1 μM, with a bell-shaped dose-response curve. Maximum cell-covered area was observed after 9-12 h after peptide addition. The optimal concentration allowing the complete coverage of the wound field was 500 μm. These data indicate that a low concentration of Esc-1a(1-21)$NH_2$ promotes the closure of a wound field produced in a hTCEpi monolayer. This finding suggests that, Esc-1a(1-21)$NH_2$ may facilitate healing of corneal epithelial injuries in vivo.

EXAMPLE 7

In Vitro Anti-endotoxin Activity of Esc-1a(1-21)$NH_2$

Macrophages (Raw 264.7) were cultured overnight in 96-well plates ($1\times10^5$ cells/well) in DMEM supplemented with 4 mM L-glutamine, 1 mM sodium pyruvate, MEM and 10% FBS. The medium was then removed and replaced with fresh medium containing LPS (10 ng/ml final concentration) and the peptide at different concentrations. Cells were incubated at 37° C. for 4 h, after which the medium was collected and TNF-α concentration in the samples was evaluated using a mouse TNF-α enzyme-linked immunosorbant assay kit according to the manufacturer's protocol (ELISA, Biosource). Cells that were stimulated with LPS alone, and untreated cells served as controls. All experiments were done in triplicate.

Figure 10:
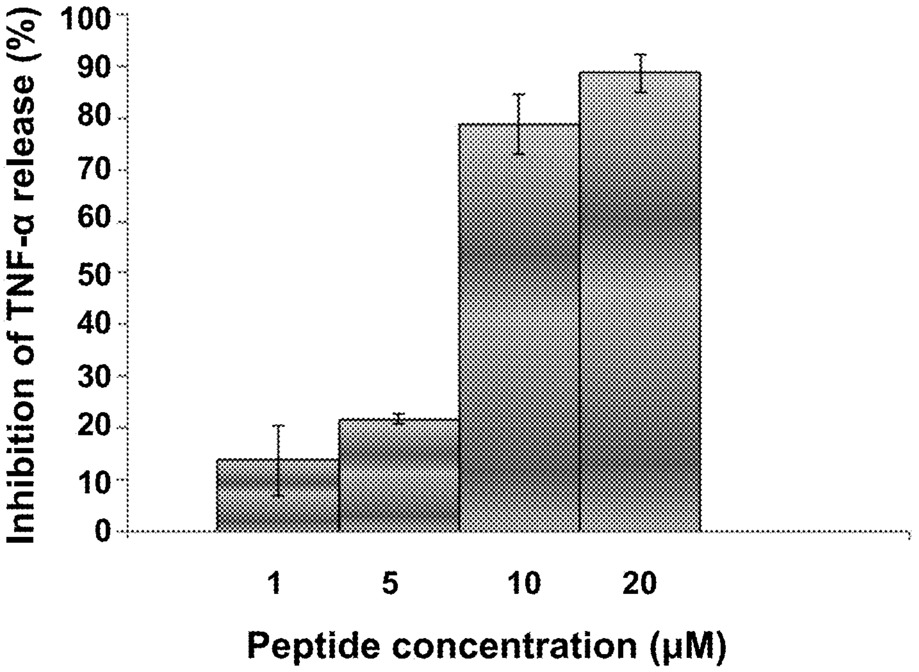
FIG. 10 shows the effect of different concentrations of Esc-1a(1-21)$NH_2$ in inhibiting the secretion of the pro-inflammatory cytokine TNF-α from LPS-stimulated murine macrophages. RAW264.7 cells were stimulated with LPS (10 ng/ml) derived from *P. aeruginosa* 10 in the presence of 1, 5, 10 and 20 μM Esc-1a(1-21)$NH_2$ for 4 hours at 37° C. and 5% $CO_2$. The percentage of inhibition of TNF-α release was normalized to that of macrophages stimulated with LPS without peptide (0% inhibition). The results are the average of three independent experiments ±S.D. A clear concentration-dependent effect on the inhibition of TNF-α extracellular release was observed with ~80% and 90% inhibition of cytokine secretion, at 10 μM and 20 μM, respectively.

These data (FIG. 10) show that Esc-1a(1-21)$NH_2$ is able to dampen down inflammatory cytokine production induced by bacterial products. Thus, not only may Esc-1a(1-21)$NH_2$ reduce severity of bacterial keratitis by directly killing invading organisms (FIGS. 1-6), it may also help reduce corneal damage caused by damaging cytokines produced by host cells as part of the natural inflammatory response.

EXAMPLE 8

In Vitro Viability Assay of Esc-1a(1-21)$NH_2$ and its Diastereomer Esc(1-21)-1c on Other Mammalian Cells (Human Type II Alveolar Epithelial Cell Line A549 and Murine Macrophages Raw 264.7)

Cells were plated in wells of a microtiter plate, at $4\times10^4$ cells/well in DMEM supplemented with 4 mM glutamine and 2% FBS (for A549 cells) or DMEM containing 4 mM glutamine, MEM, sodium pyruvate and 2% FBS (for Raw 264.7 macrophages). After overnight incubation at 37° C. in a 5% $CO_2$ atmosphere, the medium was replaced with 100 μl fresh serum-free medium supplemented with the peptides at different concentrations. After 24 h of peptide treatment, cell viability was determined by a MTT assay. The experimental procedure was similar to that described in Example 3.

Figure 11A:
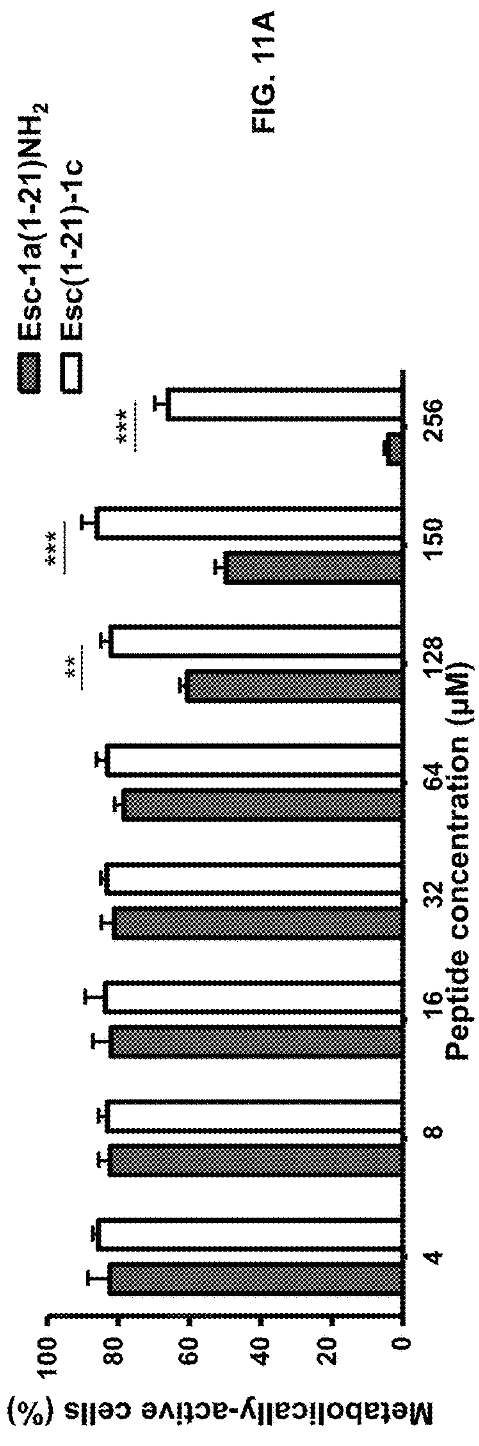
FIGS. 11A-11B shows the peptides' effect on the viability of A549 cells and Raw 264.7 macrophages. Cell viability is expressed as percentage with respect to the control (cells not treated with the peptides). Data points represent the mean of triplicate samples ±SEM. When the peptides were tested for their effect on the viability of A549 cells (FIG. 11A), they did not cause a significant reduction in the amount of living cells at a concentration of 64 μM and below. However, a significant difference was found between the two isomers at higher concentrations, with an $LD_{50}$ of 150 μM or >256 μM for the wild type Esc-1a(1-21)$NH_2$ or the diastereomer Esc(1-21)-1c, respectively. This discrepancy was even more pronounced against macrophages: Esc-1a(1-21)$NH_2$ had an $LD_{50}$ of 64 μM and was highly toxic (100% killing) at 128 μM after 24 h incubation, while Esc(1-21)-1c caused only ~20% decrease in the percentage of metabolically-active cells at the highest concentration of 256 μM (FIG. 11B). The levels of statistical significance between the two peptides are indicated as follows: $p<0.01$, *$p<0.001$.
Figure 11B:
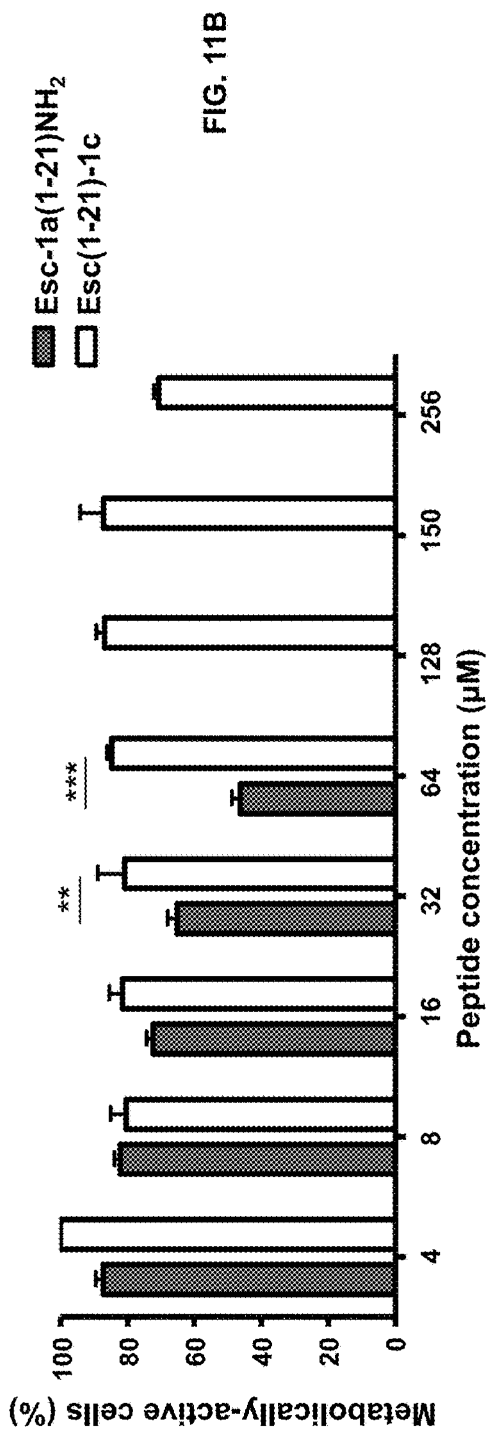

The data in FIGS. 11A-11B show that low concentrations of the peptides are not toxic to lung cells or murine macrophages, higher concentrations of Esc-1a(1-21)$NH_2$ are however toxic. This is comparable to the findings for human corneal epithelial cells (FIG. 4). Notably diastereomer Esc(1-21)-1c, obtained by replacing L-Leu 14 and L-Ser 17 with the corresponding D enantiomers, did not exhibit significant toxicity even at high concentrations. The reduced toxicity of this diastereomer means it may have greater potential as a therapeutic than the wild type peptide.

EXAMPLE 9

In Vitro Visibility Assay of Esc-1a(1-21)$NH_2$ and its Enantiomer Composed of all D Amino Acids on Human Immortalized Keratinocytes (HaCaT Cell Line)

Figure 12A:
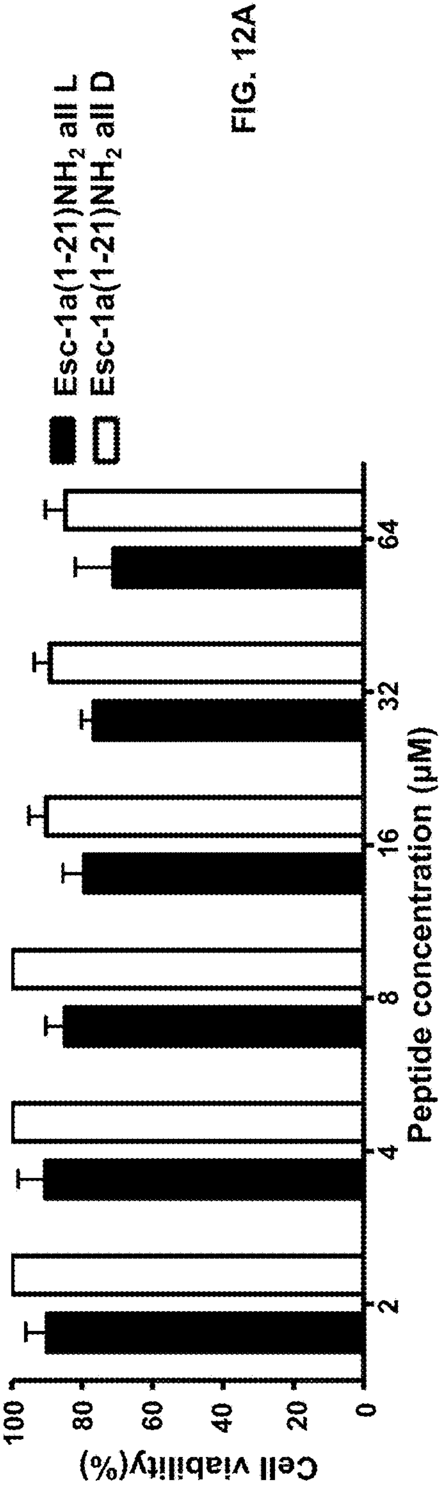
FIGS. 12A-12B show the peptides' effect on the viability of HaCaT keratinocytes. Cell viability is expressed as percentage with respect to the control (cells not treated with the peptide). Data points represent the mean of triplicate samples ±SEM. Both peptides did not show any remarkable reduction in the number of metabolically-active keratinocytes, after 2 h treatment at concentrations in the range of 1-64 μM, and the difference between them was not statistically significant (FIG. 12A). In contrast, 24 h after peptide addition, only the all-L peptide was slightly toxic at 32 μM and 64 μM (FIG. 12B), causing approximately 20% reduction in the percentage of metabolically-active cells compared to the all D Esc-1a(1-21)$NH_2$ ($p<0.001$). The levels of statistical significance between the two peptides are indicated as follows: ***$p<0.001$.
Figure 12B:
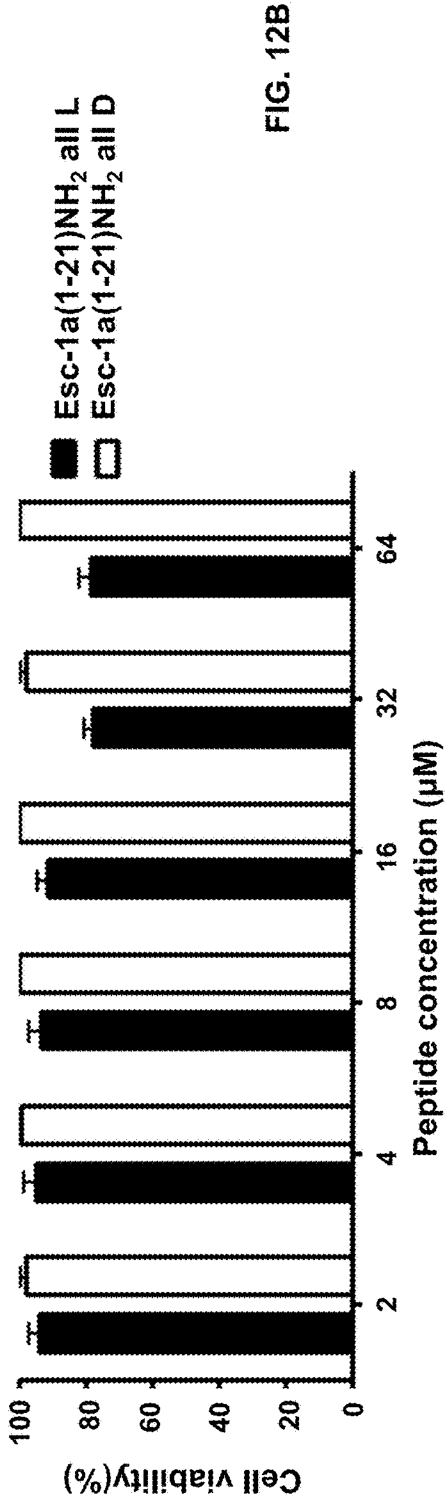

The experimental procedure was similar to that described in Example 8, for A549 cells, with the exception of incubation time with the peptide (2 hours and 24 hours). As with other investigations in to cytotoxicity, the peptides became toxic only at the higher concentrations tested (FIG. 12A-12B). The all D enantiomer did not show toxicity at the higher concentration indicating a potential benefit over the wild type peptide.

EXAMPLE 10

Effect of Esc-1a(1-21)$NH_2$ and its Diastereomer Esc(1-21)-1c on Wound Healing of A549 Cells The experimental procedure was similar to that described in Example 6 with the following three differences: (i) number of cells seeded on each side of the ibidi culture inserts (40,000 cells suspended in DMEM supplemented with 4 mM glutamine and 10% FBS instead of 70,000 cells in KGM-2g as for corneal epithelial cells); (ii) FBS percentage in the medium used for the wound healing assay (2% instead of 5% as for corneal epithelial cells); (iii) time intervals at which wound fields were visualized (15, 20 and 24 h instead of 3, 6, 9 and 12 h as for corneal epithelial cells).

Figure 13A:
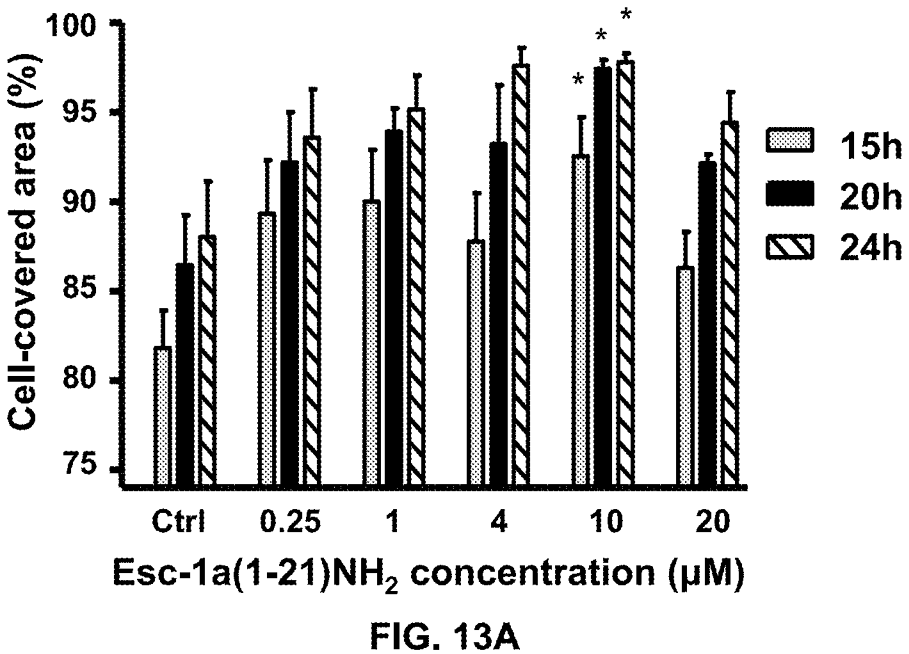
FIGS. 13A-13B shows the peptides' effect on the closure of a wound field produced in a monolayer of A549 lung epithelial cells. The percentage of cell-covered area at each time point is reported on the y-axis. Control (Ctrl) represents cells not treated with the peptides. All data are the mean of at least three independent experiments ±SEM. The levels of statistical significance between Ctrl and treated samples are indicated as follows: *, $p<0.05$, , $p<0.01$. Both peptides were able to stimulate the closure of the gap produced in the monolayer of A549 cells, with the optimal concentration allowing the almost complete coverage of the wound field equal to 10 μM (for the wild type peptide, FIG. 13A) or 4 μM (for the diastereomer, FIG. 13**B) within approximately 24 hours or 20 hours, respectively. This suggests a higher effectiveness of the diastereomer in promoting migration of lung epithelial cells.
Figure 13B:
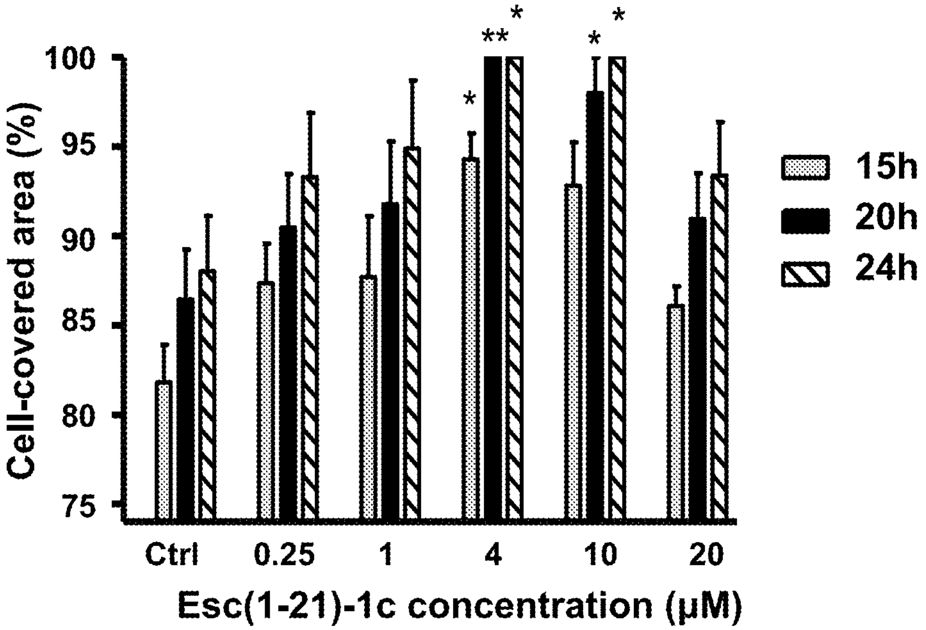

As shown in FIGS. 13A-13B, Esc-1a(1-21)$NH_2$ and its diastereomer both stimulated wound closure although at concentrations much higher than were required to induce a similar effect in human corneal epithelial cells. This may reflect cell specific differences.

EXAMPLE 11

Effect of Esc-1a(1-21)$NH_2$ and its Enantiomer on Wound Healing of HaCaT Cells

Figure 14A:
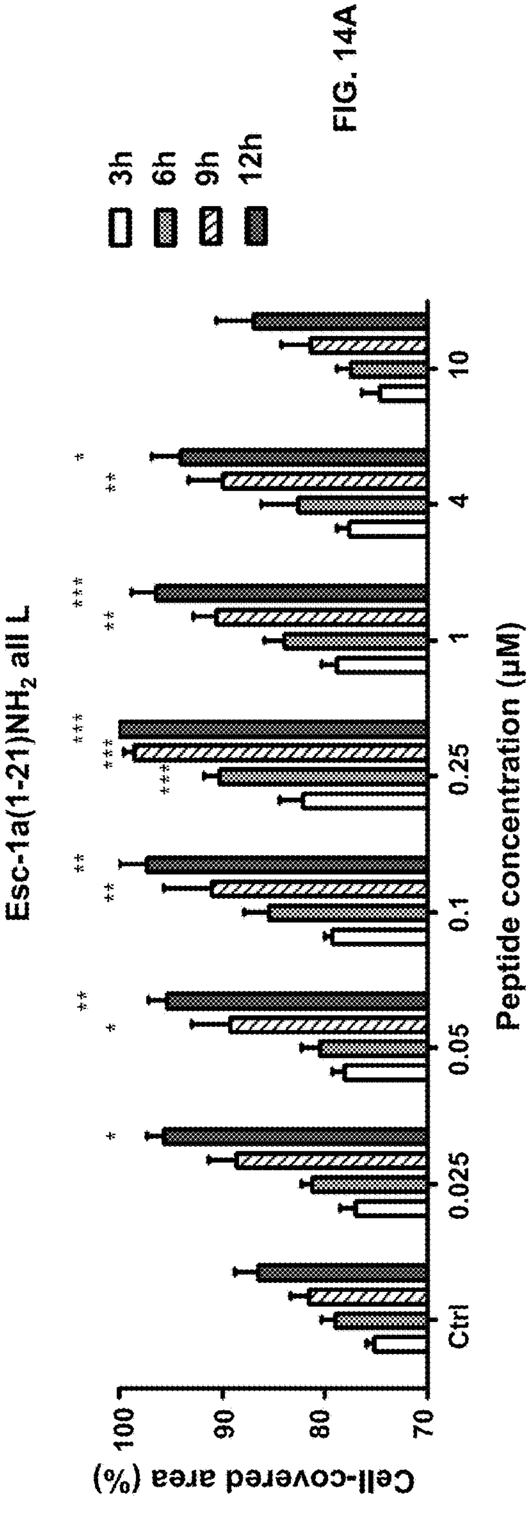
FIGS. 14A-14B shows the peptides' effect on the closure of a "wound field" produced in a monolayer of HaCaT cells. The percentage of cell-covered area at each time point is reported on the y-axis. Control (Ctrl) represents cells not treated with the peptide. All data are the mean of at least three independent experiments ±SEM. The levels of statistical significance between Ctrl and treated samples are indicated as follows: *$p<0.05$; $p<0.01$; *$p<0.001$. The all-L peptide was found to induce coverage of the "wound-field" in about 9-12 h with a bell-shaped dose-response curve (FIG. 14A). The optimal concentration allowing gap closure was 0.25 μM. On the contrary, no statistically significant difference in the cell-covered area was measured between the all-D Esc(1-21)-treated samples and the untreated control cells (FIG. 14 B).
Figure 14B:
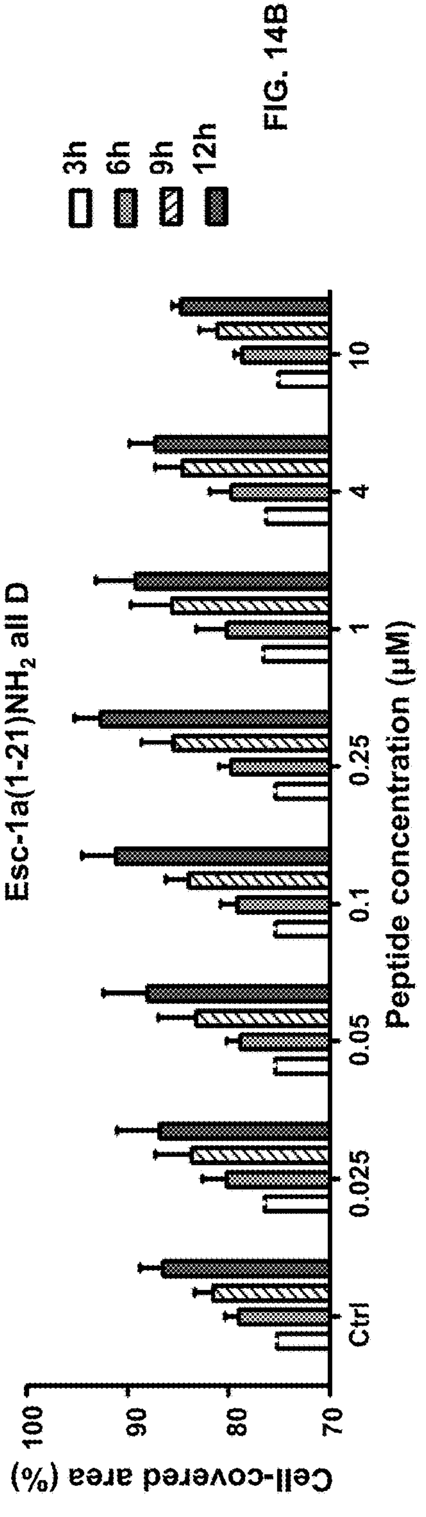

The experimental procedure is similar to that described in Example 6 with the following two differences: (i) 40,000 cells suspended in DMEM supplemented with 4 mM glutamine and 10% FBS were seeded on each side of the ibidi culture inserts instead of 70,000 cells in KGM-2g as for corneal epithelial cells; (ii) serum-free medium was used in the wound healing assay instead of medium supplemented with 5% FBS as for corneal epithelial cells. The results (FIGS. 14A-14B) show that Esc-1a(1-21)$NH_2$ can stimulate wound closure in HaCaT cell monolayers however this is not the case for its enantiomer. Overall, the experiments indicate that Esc-1a(1-21)$NH_2$ can stimulate wound closure in different types of mammalian cells but this is with a different kinetic or optimal concentration and thus a stereospecific mechanism involving a direct/indirect activation of different signalling transduction cascades (depending on the selected cell type) likely subtends such events.

EXAMPLE 12

Effect of Serum on the Stability of Esc-1a(1-21)$NH_2$ and its Diastereomer Esc(1-21)-1c A total of 125 μl of a 0.92 mM solution of each peptide was incubated at 37° C. with 20 μl and 60 μl human serum. Samples were collected after 5 h and 24 h of incubation, precipitated with 200 μl methanol, and centrifuged for 2 min at 10,000 g. The crude solution was then analyzed by high-performance liquid chromatography (HPLC) and mass spectrometry. HPLC was performed with a Vydac C18 column, and the crude solution was diluted 5 times with 0.1% trifluoroacetic acid before injection and monitored at 280 nm.

Table 3 shows that there is less degradation of the D-amino acids containing diastereomer, especially after 24 h incubation. Indeed, the amount of this peptide was reduced to 45.61% or 25.46% from the initial amount, in 10% or 30% serum respectively, while the estimated percentage remaining of the wild-type Esc-1a(1-21)$NH_2$ was approximately 22.19% or 11.5%, respectively.

Compared to other naturally-occurring AMPs with a simple structure and whose half life is approximately 1-2 hours, Esc-1a(1-21)$NH_2$ is revealed to be a peptide with good stability, even when containing all L-amino acids. This suggests that in addition to topical ocular surface application Esc(1-21) has potential for use as a systemic therapeutic.

TABLE 3

Peptide amount in 10% & 30% human fresh serum after 5 h & 24 h incubation at 37° C.

| Peptide designation | Peptide Sequence | Peptide Amount (%) 5 h 10% Serum | 5 h 30% Serum | 24 h 10% Serum | 24 h 30% Serum |
|---|---|---|---|---|---|
| Esc-1a (1-21)NH2 | GIFSKLAGKKIKNLLISGLKG-$NH_2$ (SEQ ID NO: 2) | 44.40 | 20.95 | 22.19 | 11.5 |
| Esc-1a (1-21)-1cNH2 | GIFSKLAGKKIKN*L*LI*S*GLKG-$NH_2$ (SEQ ID NO: 3) | 63.34 | 30.12 | 45.61 | 25.46 |

[a] D amino acids are in italics and underlined

[b]Peptide amounts were determined by the peak areas of the RP-HPLC relative to those of the control peptide (dissolved in PBS) at 0 min (set as 100%).

What is claimed is:

1. A method for reducing the severity of microbe-induced inflammation, comprising the step of contacting a bacteria, a fungus, or an acanthamoeba with a synthetic antibacterial peptide consisting of the sequence shown in SEQ ID NO: 3, or a pharmaceutical composition comprising the antibacterial peptide, wherein said contacting step comprises an effective amount of the antibacterial peptide effective to reduce microbe-induced inflammation or inhibit growth of said bacteria, said fungus, or said acanthamoeba.

2. The method of claim 1, wherein said synthetic antibacterial peptide reduces cytokine production induced by said bacteria, said fungus, or said acanthamoeba and increases anti-inflammatory cytokine production from host immune cells.

3. The method of claim 1, where said bacteria is a gram negative bacteria selected from the group consisting of *Escherichia coli, Salmonella, Shigella, Pseudomonas, Moraxella, Helicobacter, Stenotrophomonas, Bdellovibrio*, acetic acid bacteria, *Legionella, Wolbachia, Neisseria gonorrhoeae, Neisseria meningitidis, Moraxella catarrhalis, Hemophilus influenzae, Klebsiella pneumoniae, Legionella pneumophila, Pseudomonas aeruginosa, Helicobacter pylori, Salmonella enteritidis, Salmonella typhi* and *Acinetobacter baumannii.*

4. The method of claim 1, where said bacteria is a gram positive bacteria selected from the group consisting of *Streptococcus, Staphylococcus, Corynebacterium, Listeris, Bacillus*, and *Clostridium.*

5. The method of claim 1, further comprising the step of contacting said bacteria, said fungus, or said acanthamoeba with one or more of an antibacterial compound, an anti-acanthamoebal compound, or an antifungal compound.

6. The method of claim 5, wherein the antibacterial compound is one or more of an aminoglycoside, a beta-lactam, a cephalosporin, a quinolone, a macrolide, an oxazolidinone, an ansamycin, a sulphonamide, a tetracycline, a glycopeptide, a parahydroxy benzoic acid ester, sulfisoxazole, trimethoprim, novobiocin, daptomycin and linezolid.

7. The method of claim 5, wherein the antifungal compound is one or more of an azole, a macrocycle, an allyl amine, an echinocandin, polygodial, ciclopirox, tolnaftate, benzoic acid, undecylenic acid, flucytosine and griseofulvin.

8. The method of claim 5, wherein said anti-acanthamoebal compound is one or more of a ketoconazole, fluconazole, sulfadiazine, pentamidine, isethionate, amphotericin B, azithromycin, itraconazole and rifampicin.

9. The method of claim 1, wherein said synthetic antibacterial peptide is in the form of a solid, an ointment, a gel, a liquid, an aerosol, a mist, a polymer, a contact lens, a film, an emulsion, or a suspension.

10. The method of claim 1, wherein said pharmaceutical composition is administered topically.

11. The method of claim 1, wherein said synthetic antibacterial peptide is incorporated into a sustained-release carrier.

12. The method of claim 11, wherein said sustained-release carrier is selected from the group consisting of a sustained release polymer, a nanoparticle, a nanosuspension, a liposome and a microcapsule.

* * * * *